US010050161B2

(12) United States Patent
Ono et al.

(10) Patent No.: US 10,050,161 B2
(45) Date of Patent: Aug. 14, 2018

(54) SEMICONDUCTOR FILM, METHOD OF PRODUCING SEMICONDUCTOR FILM, SOLAR CELL, LIGHT-EMITTING DIODE, THIN FILM TRANSISTOR, AND ELECTRONIC DEVICE

(71) Applicant: FUJIFILM Corporation, Tokyo (JP)

(72) Inventors: Masashi Ono, Kanagawa (JP); Makoto Kikuchi, Kanagawa (JP); Atsushi Tanaka, Kanagawa (JP); Masayuki Suzuki, Kanagawa (JP); Yoshihiko Kanemitsu, Kyoto (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 14/699,817

(22) Filed: Apr. 29, 2015

(65) Prior Publication Data

US 2015/0236178 A1     Aug. 20, 2015

Related U.S. Application Data

(63) Continuation of application No. PCT/JP2013/077668, filed on Oct. 10, 2013.

(30) Foreign Application Priority Data

Oct. 31, 2012  (JP) ................................ 2012-241230
Dec. 26, 2012  (JP) ................................ 2012-282431

(51) Int. Cl.
*H01L 31/0352*  (2006.01)
*H01L 31/0304*  (2006.01)
(Continued)

(52) U.S. Cl.
CPC ........ *H01L 31/035218* (2013.01); *C07F 7/24* (2013.01); *C07F 9/06* (2013.01);
(Continued)

(58) Field of Classification Search
CPC ........... H01L 21/0254; H01L 21/02546; H01L 21/02549; H01L 21/02568;
(Continued)

(56) References Cited

U.S. PATENT DOCUMENTS

2004/0007169 A1    1/2004  Ohtsu et al.
2011/0006281 A1*   1/2011  Jang ...................... B82Y 30/00
                                                          257/13
2013/0146834 A1*   6/2013  Cho .................. H01L 21/02521
                                                           257/9

FOREIGN PATENT DOCUMENTS

EP    1 116 036 B1    8/2004
JP    2003-286292 A   10/2003
(Continued)

OTHER PUBLICATIONS

Tai et al., Inter-Dot Distance Dependence of Photoluminescene Properties in CdSe Quantum Dot Systems, Applied Physics Excpress 3 (2010) 035202.*
(Continued)

*Primary Examiner* — Alexandre F Ferre
(74) *Attorney, Agent, or Firm* — Birch, Stewart, Kolasch & Birch, LLP

(57) ABSTRACT

A semiconductor film, including: an assembly of semiconductor quantum dots containing a metal atom; and at least one ligand that is coordinated to the semiconductor quantum
(Continued)

dots and that is selected from a ligand represented by Formula (A), a ligand represented by Formula (B), and a ligand represented by Formula (C):

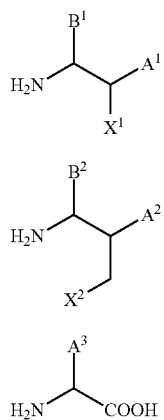

Formula (A)

Formula (B)

Formula (C)

wherein, in Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH; in Formula (B), $X^2$ represents —SH, —NH$_2$, or —OH; and each of $A^2$ and $B^2$ independently represents a hydrogen atom or a substituent having from 1 to 10 atoms; and in Formula (C), $A^3$ represents a hydrogen atom or a substituent having from 1 to 10 atoms.

25 Claims, 10 Drawing Sheets

(51) Int. Cl.
| | |
|---|---|
| *H01L 31/032* | (2006.01) |
| *H01L 33/00* | (2010.01) |
| *H01L 33/06* | (2010.01) |
| *H01L 33/30* | (2010.01) |
| *H01L 33/32* | (2010.01) |
| *H01L 33/26* | (2010.01) |
| *H01L 29/786* | (2006.01) |
| *H01L 29/06* | (2006.01) |
| *H01L 29/12* | (2006.01) |
| *H01L 29/66* | (2006.01) |
| *H01L 21/02* | (2006.01) |
| *C07F 7/24* | (2006.01) |
| *C07F 9/06* | (2006.01) |
| *H01L 31/18* | (2006.01) |

(52) U.S. Cl.
CPC .... *H01L 21/0254* (2013.01); *H01L 21/02546* (2013.01); *H01L 21/02549* (2013.01); *H01L 21/02568* (2013.01); *H01L 21/02601* (2013.01); *H01L 21/02628* (2013.01); *H01L 29/0665* (2013.01); *H01L 29/122* (2013.01); *H01L 29/66742* (2013.01); *H01L 29/66969* (2013.01); *H01L 29/78681* (2013.01); *H01L 29/78696* (2013.01); *H01L 31/0304* (2013.01); *H01L 31/0324* (2013.01); *H01L 31/03044* (2013.01); *H01L 31/18* (2013.01); *H01L 31/184* (2013.01); *H01L 31/1856* (2013.01); *H01L 33/0062* (2013.01); *H01L 33/0075* (2013.01); *H01L 33/0091* (2013.01); *H01L 33/06* (2013.01); *H01L 33/26* (2013.01); *H01L 33/30* (2013.01); *H01L 33/32* (2013.01); *Y10S 977/774* (2013.01); *Y10T 428/249921* (2015.04); *Y10T 428/268* (2015.01)

(58) Field of Classification Search
CPC ......... H01L 21/02601; H01L 21/02628; H01L 29/0665; H01L 29/122; H01L 29/66742; H01L 29/66969; H01L 29/78681; H01L 29/78696; H01L 31/0304; H01L 31/03044; H01L 31/0324; H01L 31/035218; H01L 31/18; H01L 31/184; H01L 31/1856; H01L 33/0062; H01L 33/0075; H01L 33/0091; H01L 33/06; H01L 33/26; H01L 33/30; H01L 33/32
See application file for complete search history.

(56) References Cited

FOREIGN PATENT DOCUMENTS

| JP | 2004-315661 A | 11/2004 |
|---|---|---|
| JP | 4425470 B2 | 3/2010 |
| WO | WO 2011/005023 A2 | 1/2011 |

OTHER PUBLICATIONS

Geyer et al., "Charge transport in mixed CdSe and CdTe colloidal nanocrystal films", The American Physical Society, Physical Review B 82, 2010, pp. 155201-1-155201-8.
International Search Report issued in PCT/JP2013/077668, dated Nov. 12, 2013.
Luther et al., "Structural, Optical, and Electrical Properties of Self-Assembled Films of PbSe Nanocrystals Treated with 1,2-Ethanedithiol", American Chemical Society, Jan. 31, 2008, vol. 2, No. 2, pp. 271-280.
PCT/ISA/237—Issued in PCT/JP2013/077668, dated Nov. 12, 2013.
Japanese Office Action dated Jul. 5, 2016, for Japanese Application No. 2012-282431 with the English translation.

* cited by examiner

BF(BRIGHT FIELD)-STEM         HAADF(HIGH ANGLE ANNULAR DARK FIELD)-STEM

BF(BRIGHT FIELD)-STEM         HAADF(HIGH ANGLE ANNULAR DARK FIELD)-STEM

SEMICONDUCTOR FILM, METHOD OF PRODUCING SEMICONDUCTOR FILM, SOLAR CELL, LIGHT-EMITTING DIODE, THIN FILM TRANSISTOR, AND ELECTRONIC DEVICE

CROSS-REFERENCE TO RELATED APPLICATIONS

This application is a continuation application of International Application No. PCT/JP2013/077668, filed Oct. 10, 2013, the disclosure of which is incorporated herein by reference in its entirety. Further, this application claims priority from Japanese Patent Application No. 2012-241230, filed Oct. 31, 2012, and Japanese Patent Application No. 2012-282431, filed Dec. 26, 2012, the disclosures of which are incorporated herein by reference in their entirety.

TECHNICAL FIELD

The present invention relates to a semiconductor film, a method of producing a semiconductor film, a solar cell, a light-emitting diode, a thin film transistor, and an electronic device.

BACKGROUND ART

In recent years, the research on high efficiency solar cells called the third generation solar cells has flourished. Among others, solar cells that use colloidal quantum dots have been reported to be, for example, capable of increasing the quantum efficiency as a result of a multi-exciton generation effect, and thus attention has been paid to them. However, in solar cells that use colloidal quantum dots (also referred to as quantum dot solar cells), the conversion efficiency is about 7% at the maximum, and there is a demand for a further increase in the conversion efficiency.

In such a quantum dot solar cell, a semiconductor film formed from an assembly of quantum dots plays the role of a photoelectric conversion layer, therefore, research on semiconductor films themselves that are formed from a quantum dot assembly is also being conducted actively.

For example, semiconductor nanoparticles that use a relatively long ligand having a hydrocarbon group having 6 or more carbon atoms have been disclosed (see, for example, Patent Document 1 (Japanese Patent No. 4425470)).

Regarding the technique for improving the characteristics of a semiconductor film formed from a quantum dot assembly, it has been reported that when the ligand molecule bound to a quantum dot (for example, about 2 nm to 10 nm) is replaced with a shorter ligand molecule, electrical conductivity is enhanced (see, for example, Non-Patent Document 1 (S. Geyer, et al., "Charge transport in mixed CdSe and CdTe colloidal nanocrystal films", Physical Review B (2010)) and Non-Patent Document 2 (J. M. Luther, et al., "Structural, Optical, and Electrical Properties of Self-Assembled Films of PbSe Nanocrystals Treated with 1,2-Ethanedithiol", ACS Nano (2008))). It has been reported in Non-Patent Document 2 that when the oleic acid (molecular chain length: about 2 nm to 3 nm) around the quantum dots of PbSc is replaced with ethanedithiol (molecular chain length: 1 nm or less), quantum dots are brought into close proximity to one another, and electrical conductivity is enhanced.

SUMMARY OF INVENTION

Technical Problem

However, since the semiconductor film described in Patent Document 1 has a large ligand, and the close proximity between semiconductor quantum dots is insufficient, excellent photoelectric conversion characteristics are not obtained. Even in a case in which the butylamine used in Non-Patent Document 1 or the ethanedithiol used in Non-Patent Document 2 is used as a ligand, for example, according to Non-Patent Document 1, a photoelectric current value of only about several hundred nanoamperes (nA) can be obtained at the maximum. Also, when ethanedithiol is used as a ligand, flaking of the semiconductor film may easily occur.

It is an object of the invention to provide a semiconductor film in which a high photoelectric current value is obtained and film flaking is suppressed, and a method of production thereof.

Furthermore, it is another object of the invention to provide a solar cell, a light-emitting diode, a thin film transistor and an electronic device, in each of which a high photoelectric current value is obtained and film flaking is suppressed.

Solution to Problem

In order to achieve the above objects, the following invention is provided.

<1> A semiconductor film, comprising:
an assembly of semiconductor quantum dots containing a metal atom; and
at least one ligand that is coordinated to the semiconductor quantum dots and that is selected from the group consisting of a ligand represented by the following Formula (A), a ligand represented by the following Formula (B), and a ligand represented by the following Formula (C):

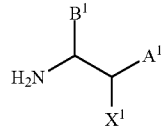

Formula (A)

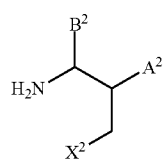

Formula (B)

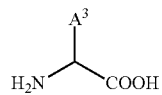

Formula (C)

wherein, in Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH;

in Formula (B), $X^2$ represents —SH, —NH$_2$, or —OH; and each of $A^2$ and $B^2$ independently represents a hydrogen atom or a substituent having from 1 to 10 atoms; and in Formula (C), $A^3$ represents a hydrogen atom or a substituent having from 1 to 10 atoms.

<2> The semiconductor film according to <1>, wherein each of $A^1$, $B^1$, $A^2$, $B^2$, and $A^3$ independently represents a hydrogen atom or a substituent having 7 or fewer atoms.

<3> The semiconductor film according to <1> or <2>, wherein $A^1$, $B^1$, $A^2$, $B^2$, and $A^3$ are hydrogen atoms.

<4> The semiconductor film according to any one of <1> to <3>, wherein the at least one ligand is at least one selected from the group consisting of 2-aminoethanethiol, 2-aminoethanol, 3-amino-1-propanol, a 2-aminoethanethiol derivative, a 2-aminoethanol derivative, and a 3-amino-1-propanol derivative.

<5> The semiconductor film according to any one of <1> to <4>, wherein the at least one ligand is represented by Formula (A) and forms a 5-membered ring chelate together with the metal atom in the semiconductor quantum dots.

<6> The semiconductor film according to any one of <1> to <5>, wherein a complex stability constant $\log \beta_1$ between the at least one ligand and the metal atom of the semiconductor quantum dots is 8 or higher.

<7> The semiconductor film according to any one of <1> to <6>, wherein the semiconductor quantum dots have an average shortest interdot distance of less than 0.45 nm.

<8> The semiconductor film according to <7>, wherein the semiconductor quantum dots have an average shortest interdot distance of less than 0.30 nm.

<9> The semiconductor film according to <7> or <8>, wherein the semiconductor quantum dots have an average shortest interdot distance of less than 0.20 nm.

<10> The semiconductor film according to any one of <1> to <9>, wherein the semiconductor quantum dots contain at least one selected from the group consisting of PbS, PbSe, InN, InAs, InSb, and InP.

<11> The semiconductor film according to any one of <1> to <10>, wherein the semiconductor quantum dots have an average particle diameter of from 2 nm to 15 nm.

<12> The semiconductor film according to <10> or <11>, wherein the semiconductor quantum dots contain PbS.

<13> A method of producing a semiconductor film, the method comprising:

a semiconductor quantum dot assembly forming step of applying, onto a substrate, a semiconductor quantum dot dispersion liquid containing semiconductor quantum dots containing a metal atom, a first ligand coordinated to the semiconductor quantum dots, and a first solvent, and thereby forming an assembly of the semiconductor quantum dots; and a ligand exchange step of applying, to the assembly of the semiconductor quantum dots, a solution containing a second solvent and a second ligand that has a shorter molecular chain length than the first ligand and that is at least one selected from the group consisting of a ligand represented by the following Formula (A), a ligand represented by the following Formula (B), and a ligand represented by the following Formula (C), and thereby exchanging the first ligand coordinated to the semiconductor quantum dots with the second ligand:

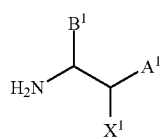

Formula (A)

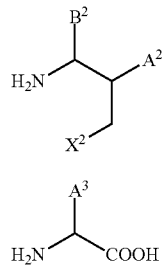

wherein, in Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH;

in Formula (B), $X^2$ represents —SH, —NH$_2$, or —OH; and each of $A^2$ and $B^2$ independently represents a hydrogen atom or a substituent having from 1 to 10 atoms; and in Formula (C), $A^3$ represents a hydrogen atom or a substituent having from 1 to 10 atoms.

<14> The method of producing a semiconductor film according to <13>, wherein the first ligand is a ligand having a main chain having 6 or more carbon atoms.

<15> The method of producing a semiconductor film according to <13> or <14>, wherein each of the semiconductor quantum dot assembly forming step and the ligand exchange step is carried out two or more times.

<16> The method of producing a semiconductor film according to any one of <13> to <15>, wherein each of $A^1$, $B^1$, $A^2$, $B^2$, and $A^3$ independently represents a hydrogen atom or a substituent having 7 or fewer atoms.

<17> The method of producing a semiconductor film according to any one of <13> to <16>, wherein $A^1$, $B^1$, $A^2$, $B^2$, and $A^3$ are hydrogen atoms.

<18> The method of producing a semiconductor film according to any one of <13> to <17>, wherein the second ligand is at least one selected from the group consisting of 2-aminoethanethiol, 2-aminoethanol, 3-amino-1-propanol, a 2-aminoethanethiol derivative, a 2-aminoethanol derivative, and a 3-amino-1-propanol derivative.

<19> The method of producing a semiconductor film according to any one of <13> to <18>, wherein, in the ligand exchange step, the second ligand is represented by Formula (A) and forms a 5-membered ring chelate together with the metal atom in the semiconductor quantum dots.

<20> The method of producing a semiconductor film according to any one of <13> to <19>, wherein the semiconductor quantum dots contain at least one selected from the group consisting of PbS, PbSe, InN, InAs, InSb, and InP.

<21> The method of producing a semiconductor film according to any one of <13> to <20>, wherein the semiconductor quantum dots have an average particle diameter of from 2 nm to 15 nm.

<22> The method of producing a semiconductor film according to <20> or <21>, wherein the semiconductor quantum dots contain PbS.

<23> A solar cell, comprising the semiconductor film according to any one of <1> to <12>.

<24> A light-emitting diode, comprising the semiconductor film according to any one of <1> to <12>.

<25> A thin film transistor, comprising the semiconductor film according to any one of <1> to <12>.

<26> An electronic device, comprising the semiconductor film according to any one of <1> to <12>.

Advantageous Effects of Invention

According to the invention, a semiconductor film in which a high photoelectric current value is obtained and film flaking is suppressed, and a method of production thereof, are provided.

Furthermore, according to the invention, a solar cell, a light-emitting diode, a thin film transistor and an electronic device, in each of which a high photoelectric current value is obtained and film flaking is suppressed, are provided.

DESCRIPTION OF EMBODIMENTS

Figure 1:
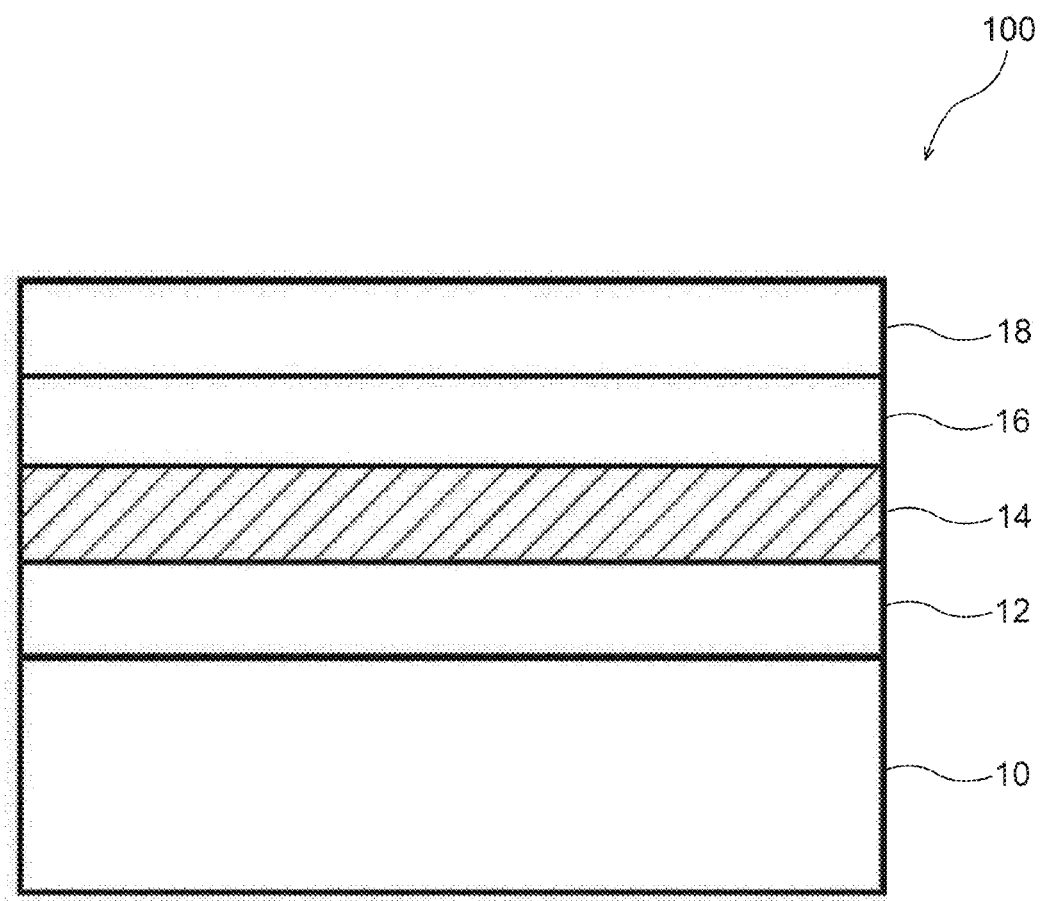
FIG. 1 is an outline diagram illustrating an example of the configuration of a p-n junction type solar cell to which the semiconductor film of the invention is applied.

Hereinafter, the semiconductor film of the invention and a method of producing the same are described in detail.
<Semiconductor Film>

The semiconductor film of the invention comprises: an assembly of semiconductor quantum dots containing a metal atom; and at least one ligand that is coordinated to the semiconductor quantum dots and that is selected from the group consisting of a ligand represented by Formula (A), a ligand represented by Formula (B), and a ligand represented by Formula (C).

Hereinafter, "at least one ligand that is selected from the group consisting of a ligand represented by Formula (A), a ligand represented by Formula (B), and a ligand represented by Formula (C)" is also referred to as a "particular ligand".

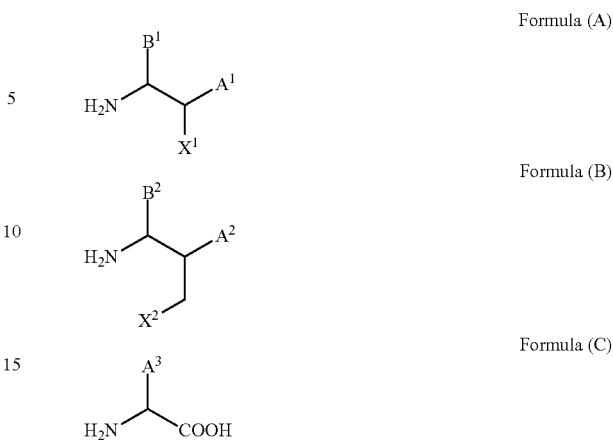

Formula (A)

Formula (B)

Formula (C)

In Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH.

In Formula (B), $X^2$ represents —SH, —NH$_2$, or —OH; and each of $A^2$ and $B^2$ independently represents a hydrogen atom or a substituent having from 1 to 10 atoms.

In Formula (C). $A^3$ represents a hydrogen atom or a substituent having from 1 to 10 atoms.

The ligand represented by Formula (A), the ligand represented by Formula (B), and the ligand represented by Formula (C) are ligands different from each other.

Semiconductor quantum dots are semiconductor particles configured to include metal atoms, and are nanometer-sized particles having a particle diameter of from several nanometers (nm) to several ten nanometers (nm).

In regard to the semiconductor film of the invention, it is speculated that since semiconductor quantum dots are linked by coordinate bonding by a particular ligand represented by Formula (A), (B), or (C) and having a small number of atoms, the distance between the semiconductor quantum dots is short. Accordingly, it is speculated that the semiconductor quantum dots are closely arranged, and the superposition of wave functions among the semiconductor quantum dots can be intensified. It is believed that as a result, electrical conductivity is increased, and the photoelectric current value can be increased.

Furthermore, the particular ligand has at least one amino group (NH$_2$) and —SH, —NH$_2$ or —OH represented by $X^1$ (or $X^2$) or OH of a carboxyl group in the molecule. The amino group is considered to have a high complex stability constant and to play the role of promoting the formation of a complex between the metal atom of the semiconductor quantum dots and —SH, —NH$_2$ or —OH represented by $X^1$ (or $X^2$) or OH of a carboxyl group. As a result, it is speculated that the connection between the semiconductor quantum dots and the particular ligand is strengthened, and thus peeling of the semiconductor film configured to include the semiconductor quantum dots and the particular ligand is suppressed.

Therefore, it is considered that the semiconductor film of the invention gives a high photoelectric current value, and flaking of the semiconductor film can be suppressed.

The semiconductor film of the invention is preferably such that the complex stability constant log $\beta_1$ between the particular ligand and the metal atom of the semiconductor quantum dots is 8 or higher.

Here, the complex stability constant is a constant determined by the relationship between a ligand and a metal atom as the object of coordinate bonding, and is represented by the following Formula (b):

$$\log \beta_1 = \frac{[ML]}{[M][L]]} \qquad \text{Formula (b)}$$

In Formula (b), [ML] represents the molar concentration of a complex formed by bonding between a metal atom and a ligand; [M] represents the molar concentration of the metal atoms that can contribute to coordinate bonding; and [L] represents the molar concentration of the ligand.

In practice, there are occasions in which plural ligands are coordinated to one metal atom; however, in this invention, the complex stability constant log $\beta_1$ represented by Formula (b) in the case in which one ligand molecule is coordinated to one metal atom, is defined as an index of the strength of coordinate bonding.

When the complex stability constant log $\beta_1$ between a particular ligand and a metal atom of a semiconductor quantum dot is 8 or more, formation of the complex is made easier.

It is preferable that the complex stability constant log $\beta_1$, is higher for a combination of a semiconductor quantum dot and a ligand. Furthermore, if the ligand is a multidentate ligand as in the case of a chelate, the strength of the bonding can be further increased. In general, when the strength of the coordinate bonding is stronger, the conventional long molecular chain ligand is replaced efficiently, and higher electrical conductivity is easily obtained. The values of the complex stability constant log $\beta_1$ of the particular ligands vary as the semiconductor quantum dot material that constitutes the semiconductor quantum dots is changed; however, since the particular ligands have short molecular chain lengths and facilitate coordination, the particular ligands can be applied to a variety of semiconductor quantum dot materials.

The value of log $\beta_1$ is more preferably 8 or higher, and still more preferably 10 or higher.

Examples of the method of determining the complex stability constant log $\beta_1$ between a particular ligand and a metal atom of a semiconductor quantum dot in the semiconductor film of the invention, include spectroscopy, magnetic resonance spectroscopy, potentiometry, solubility measurement, chromatography, calorimetry, freezing point measurement, vapor pressure measurement, relaxation measurement, viscosity measurement, and surface tension measurement.

In this invention, the complex stability constant was determined by using the Sc-Database version 5.85 (Academic Software) (2010), which summarizes various techniques and the results obtained from research institutions. If the data of log $\beta_1$ are not given in the Sc-Database version 5.85, the values described in A. E. Martell and R. M. Smith, Critical Stability Constants are used. In a case in which no data on log $\beta_1$ are described in Critical Stability Constants, the log $\beta_1$ is calculated by using the above-described measurement method, or by using a program for calculating the complex stability constant, PKAS method (A. E. Martell et al., The Determination and Use of Stability Constants, VCH (1988)).

Hereinafter, the details of the particular ligand and the semiconductor quantum dots that constitute the semiconductor film of the invention will be explained.

First, the particular ligand is explained in detail.

[At Least One Ligand Selected from Ligand Represented by Formula (A), Ligand Represented by Formula (B), and Ligand Represented by Formula (C) (Particular Ligand)]

The semiconductor film of the invention contains at least one kind of particular ligand.

The semiconductor film of the invention may also contain two or more kinds of particular ligands. That is, all of the coordinate bonds in the semiconductor quantum dot assembly contained in the semiconductor film of the invention may be bonds formed by one kind of particular ligand, or some of the coordinate bonds may be bonds formed by a particular ligand represented by Formula (A), while the rest of the coordinate bonds may be bonds formed by a particular ligand represented by Formula (B).

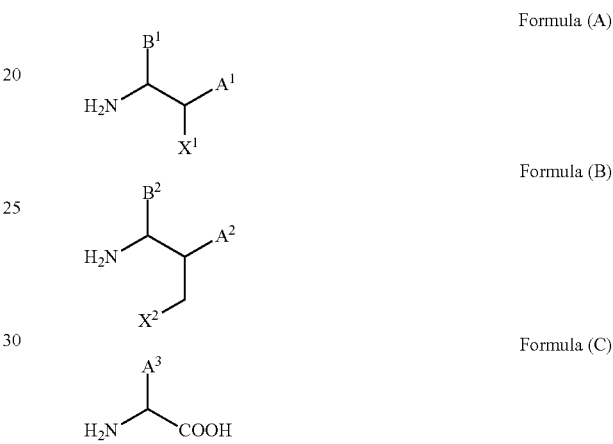

Formula (A)

Formula (B)

Formula (C)

In Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH.

In Formula (B), $X^2$ represents —SH, —NH$_2$, or —OH; and each of $A^2$ and $B^2$ independently represents a hydrogen atom or a substituent having from 1 to 10 atoms.

In Formula (C). $A^3$ represents a hydrogen atom or a substituent having from 1 to 10 atoms.

The ligand represented by Formula (A), the ligand represented by Formula (B), and the ligand represented by Formula (C) are ligands different from each other.

When each of $A^1$ and $B^1$ in Formula (A), $A^2$ and $B^2$ in Formula (B), and $A^3$ in Formula (C) represent a substituent having from 1 to 10 atoms, examples of the substituent having from 1 to 10 atoms include an alkyl group having from 1 to 3 carbon atoms [a methyl group, an ethyl group, a propyl group, or an isopropyl group], an alkenyl group having from 2 to 3 carbon atoms [an ethenyl group or a propenyl group], an alkynyl group having from 2 to 4 carbon atoms [an ethynyl group, a propynyl group, or the like], a cyclopropyl group, an alkoxy group having from 1 to 2 carbon atoms [a methoxy group or an ethoxy group], an acyl group having from 2 to 3 carbon atoms [an acetyl group or a propionyl group], an alkoxycarbonyl group having from 2 to 3 carbon atoms [a methoxycarbonyl group or an ethoxycarbonyl group], an acyloxy group having 2 carbon atoms [an acetyloxy group], an acylamino group having 2 carbon atoms [an acetylamino group], a hydroxyalkyl group having from 1 to 3 carbon atoms [a hydroxymethyl group, a hydroxyethyl group, or a hydroxypropyl group], an aldehyde group [—COH], a hydroxyl group [—OH], a carboxyl group [—COOH], a sulfo group [—SO$_3$H], a phospho group [—OPO(OH)$_2$], an amino group [—NH$_2$], a carbamoyl group [—CONH$_2$], a cyano group [—CN], an isocyanate group [—N=C=O], a thiol group [—SH], a nitro group [—NO$_2$], a nitroxy group [—ONO$_2$], an isothiocyanate group [—NCS], a cyanate group [—OCN], a thiocyanate group [—SCN], an acetoxy group [OCOCH$_3$], an acetamide group [NHCOCH$_3$], a formyl group [—CHO], a formyloxy group [—OCHO], a formamide group [—NHCHO], a sulfamino group [—NHSO$_3$H], a sulfino group [—SO$_2$H], a sulfamoyl group [—SO$_2$NH$_2$], a phosphono group [—PO$_3$H$_2$], an acetyl group [—COCH$_3$], a halogen atom [a fluorine atom, a chlorine atom, a bromine atom, or the like], and an alkali metal atom [a lithium atom, a sodium atom, a potassium atom, or the like].

If the substituent has a total number of atoms of 10 or less, the substituent may be further substituted.

When the number of atoms of the substituent is 10 or less, steric hindrance caused by the ligand can be suppressed, and semiconductor quantum dots can be brought into close proximity to one another. Therefore, high electrical conductivity of the semiconductor film can be obtained.

It is preferable that the substituent has a number of atoms of 7 or less, from the viewpoint of further shortening the distance between semiconductor quantum dots. Furthermore, it is more preferable that A$^1$, B$^1$, A$^2$, B$^2$, and A$^3$ are hydrogen atoms.

Each of X$^1$ in Formula (A) and X$^2$ in Formula (B) is preferably —OH (a hydroxyl group), from the viewpoint of solubility in a case in which the particular ligand is prepared into an alcohol solution.

Specific examples of the compound represented by Formula (A) include 2-aminoethanol, 2-aminoethane-1-thiol, 1-amino-2-butanol, 1-amino-2-pentanol, L-cysteine, and D-cysteine. Specific examples of the compound represented by Formula (B) include 3-amino-1-propanol, L-homoserine, and D-homoserine. Specific examples of the compound represented by Formula (C) include aminohydroxyacetic acid.

The particular ligand may be a derivative of a compound represented by Formula (A), a derivative of a compound represented by Formula (B), or a derivative of a compound represented by Formula (C), such as a 2-aminoethanethiol derivative, a 2-aminoethanol derivative, or a 3-amino-1-propanol derivative.

When the above-described compounds are used as the particular ligand, a higher photoelectric current value is obtained as compared with the case of using ethanedithiol as a ligand. Among them, particularly when 2-aminoethanol or 2-aminoethane-1-thiol represented by Formula (A) is used as a ligand, the effect of increasing the photoelectric current value is high.

This is speculated to be due to the following two reasons. That is, when a dangling bond (unlinked bond of an atom) of a metal atom in a semiconductor quantum dot, —NH$_2$ represented in Formula (A), and SH (or OH) represented by X$^1$ form a 5-membered ring chelate, a high complex stability constant (log β) can be obtained more easily. In addition to that, when a particular ligand is chelate coordinated to the metal atom in the semiconductor quantum dot, steric hindrance among the semiconductor quantum dots is suppressed, and as a result, high electrical conductivity is easily obtained. The mechanism of such coordination is also similarly applicable even in the case of a derivative of 2-aminoethanol or 2-aminoethanethiol. Therefore, even if a derivative of 2-aminoethanol or 2-aminoethanethiol is used, a high photoelectric current value is obtained, and high electrical conductivity is obtained.

[Assembly of Semiconductor Quantum Dots Containing Metal Atom]

The semiconductor film of the invention includes an assembly of semiconductor quantum dots. Also, the semiconductor quantum dots contain at least one kind of metal atom.

An assembly of semiconductor quantum dots refers to a form in which a large number (for example, 100 or more quantum dots in a 1-μm$^2$ square) of semiconductor quantum dots are disposed closely to one another.

The term "semiconductor" according to the invention means a substance having a specific resistance value of from 10$^{-2}$ Ωcm to 10$^8$ Ωcm.

Semiconductor quantum dots are semiconductor particles having metal atoms. According to the invention, metal atoms also include semi-metal atoms represented by a silicon (Si) atom.

Examples of the semiconductor quantum dot material that constitutes the semiconductor quantum dots include nanoparticles (particles having a size of 0.5 nm or more but less than 100 nm) of general semiconductor crystals [(a) Group IV semiconductors, (b) Group IV-IV, Group III-V, or Group II-VI compound semiconductors, and (c) compound semiconductors including combinations of three or more of Group II, Group III, Group IV, Group V, and Group VI elements]. Specific examples include semiconductor materials having relatively narrow band gaps, such as PbS, PbSe, InN, InAs, Ge, InAs, InGaAs, CuInS, CuInSe, CuInGaSe, InSb, Si, and InP.

The semiconductor quantum dots may contain at least one kind of the semiconductor quantum dot materials.

It is desirable for the semiconductor quantum dot material that the band gap in a bulk state is 1.5 eV or less. When such a semiconductor material having a relatively narrow band gap is used, high conversion efficiency can be realized in a case in which the semiconductor film of the invention is used in a photoelectric conversion layer of a solar cell.

A semiconductor quantum dot may have a core-shell structure which has a core made of a semiconductor quantum dot material and has the semiconductor quantum dot material covered with a coating compound. Examples of the coating compound include ZnS, ZnSc, ZnTe, and ZnCdS.

Among the materials described above, the semiconductor quantum dot material is desirably PbS or PbSe, in view of the ease of synthesis of semiconductor quantum dots. From the viewpoint of having less environmental burden, it is also desirable to use InN.

In the case of applying the semiconductor film of the invention to solar cell applications, it is preferable for the semiconductor quantum dots to have a narrower band gap in anticipation of an increase in the photoelectric conversion efficiency caused by a multiple exciton generation effect, which is also called a multi-exciton generation effect. Specifically, the band gap is desirably 1.0 eV or less.

From the viewpoint of further narrowing the band gap and enhancing the multi-exciton generation effect, the semiconductor quantum dot material is preferably PbS, PbSe, or InSb.

The average particle diameter of the semiconductor quantum dots is desirably from 2 nm to 15 nm. Meanwhile, the average particle diameter of the semiconductor quantum dots means the average particle diameter of ten semiconductor quantum dots. Transmission electron microscopy may be used for the measurement of the particle diameter of the semiconductor quantum dots.

Generally, semiconductor quantum dots include particles of various sizes ranging from several nanometers (nm) to several ten nanometers (nm). In regard to semiconductor quantum dots, when the average particle diameter of quantum dots is decreased to a size less than or equal to the Bohr radius of the intrinsic electron, there occurs a phenomenon in which the band gap of the semiconductor quantum dots is changed by the quantum size effect. For example, Group II-VI semiconductors have relatively large Bohr radii, and the Bohr radius of PbS is said to be about 18 nm. Furthermore, the Bohr radius of InP, which is a Group III-V semiconductor, is said to be about from 10 nm to 14 nm.

Therefore, for example, when the average particle diameter of the semiconductor quantum dots is 15 nm or less, control of the band gap by the quantum size effect is enabled.

Particularly, in the case of applying the semiconductor film of the invention to a solar cell, it is important to adjust the band gap to an optimum value by the quantum size effect, irrespective of the semiconductor quantum dot material. However, as the average particle diameter of the semiconductor quantum dots becomes smaller, the band gap increases; therefore, when the average particle diameter of the semiconductor quantum dots is 10 nm or less, greater changes in the band gap can be expected. Even if the semiconductor quantum dots are consequently narrow gap semiconductor quantum dots, since it is easier to adjust the band gap to a band gap optimal for the solar spectrum, it is more desirable that the size of the quantum dots is 10 nm or less. Furthermore, when the average particle diameter of the semiconductor quantum dots is small, and significant quantum confinement occurs, there is an advantage that an increase in the multi-exciton generation effect can be expected.

On the other hand, the average particle diameter of the semiconductor quantum dots is preferably 2 nm or more. When the average particle diameter of the semiconductor quantum dots is adjusted to 2 nm or more, the effect of quantum confinement does not become too strong, and an optimum value of the band gap may be easily obtained. Also, when the average particle diameter of the semiconductor quantum dots is adjusted to 2 nm or more, it can be made easier to control the crystal growth of the semiconductor quantum dots during the synthesis of the semiconductor quantum dots.

The semiconductor film of the invention is preferably such that the average shortest interdot distance of the semiconductor quantum dots is less than 0.45 nm.

In a film configured to contain semiconductor quantum dots, if the average shortest interdot distance of the semiconductor quantum dots is large, electrical conductivity is decreased, and thus the film becomes an insulating body. When the average shortest interdot distance of the semiconductor quantum dots is shortened, electrical conductivity is enhanced, and a semiconductor film having a high photoelectric current value is obtained.

When the semiconductor film is configured to include an assembly of semiconductor quantum dots containing a metal atom, and at least one ligand coordinated to the semiconductor quantum dots and selected from a ligand represented by Formula (A), a ligand represented by Formula (B), and a ligand represented by Formula (C), the average shortest interdot distance can be adjusted to less than 0.45 nm.

Here, the average shortest interdot distance of the semiconductor quantum dots refers to the average value of the shortest distances between the surface of a certain semiconductor quantum dot A and the surface of another semiconductor quantum dot B adjacent to the semiconductor quantum dot A (interdot shortest distances). More particularly, the average shortest interdot distance is calculated as follows.

The interdot shortest distance of the semiconductor quantum dots can be obtained by evaluating the structure of a quantum dot film containing semiconductor quantum dots by a grazing incidence small angle X-ray scattering method (GISAXS). The center-to-center distance d between adjacent semiconductor quantum dots can be obtained by such a measurement, and the interdot shortest distance is calculated by subtracting the particle diameter of a semiconductor quantum dot from the center-to-center distance d thus obtained.

When a structure evaluation of a semiconductor film is carried out using a GISAXS measuring apparatus, the average of scattered X-rays with respect to the semiconductor quantum dots existing in the entire region irradiated with X-rays is detected as the scattered X-rays for the object of measurement. The interdot shortest distance calculated based on the detected scattered X-rays is the "average shortest interdot distance" as the average value of respective interdot shortest distances.

It is speculated that as the average shortest interdot distance of the semiconductor quantum dot is smaller, the photoelectric current value of the semiconductor film can be increased. However, with a form in which the average shortest interdot distance is 0 nm, that is, the semiconductor quantum dots are in contact with one another and aggregated, the features of nanometer-sized semiconductor quantum dots are not obtained, similarly to bulk semiconductor. Therefore, the average shortest interdot distance of the semiconductor quantum dots is preferably a size exceeding 0 nm.

The average shortest interdot distance of the semiconductor quantum dots is more preferably less than 0.30 nm, and still more preferably less than 0.20 nm.

The thickness of the semiconductor film is not particularly limited: however, from the viewpoint of obtaining high electrical conductivity, the thickness is preferably 10 nm or more, and more preferably 50 nm or more. Also, from the viewpoint that there is a risk of having an excessive carrier concentration, and from the viewpoint of the ease of production, the thickness of the semiconductor film is preferably 300 nm or less.

The method of producing a semiconductor film of the invention is not particularly limited: however, from the viewpoint of further shortening the distance between the semiconductor quantum dots and thereby closely arranging the semiconductor quantum dots, it is preferable to produce the semiconductor film by the method of producing a semiconductor film of the invention.

<Method of Producing Semiconductor Film>

A method of producing a semiconductor film of the invention comprises:

a semiconductor quantum dot assembly forming step of applying, onto a substrate, a semiconductor quantum dot dispersion liquid containing semiconductor quantum dots, a first ligand coordinated to the semiconductor quantum dots, and a first solvent, and thereby forming an assembly of the semiconductor quantum dots; and a ligand exchange step of applying, to the assembly of the semiconductor quantum dots, a solution containing a second solvent and a second ligand that has a shorter molecular chain length than the first ligand and that is at least one selected from the group consisting of a ligand represented by Formula (A), a ligand represented by Formula (B), and a ligand represented by Formula (C), and thereby exchanging the first ligand coordinated to the semiconductor quantum dots with the second ligand.

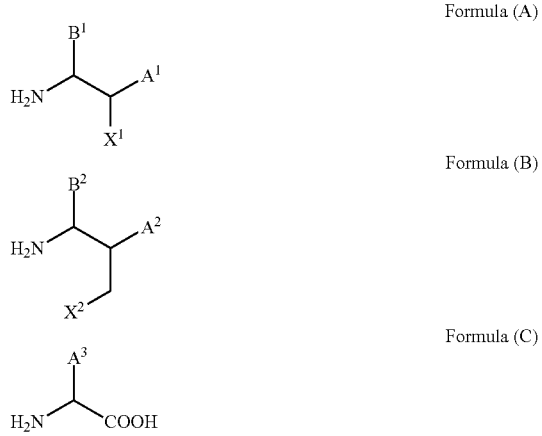

In Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH.

In Formula (B). $X^2$ represents —SH, —NH$_2$, or —OH; and each of $A^2$ and $B^2$ independently represents a hydrogen atom or a substituent having from 1 to 10 atoms.

In Formula (C), $A^3$ represents a hydrogen atom or a substituent having from 1 to 10 atoms.

In the method of producing a semiconductor film of the invention, the semiconductor quantum dot assembly forming step and the ligand exchange step may be carried out repeatedly, and the method may further include a dispersion liquid drying step of drying a semiconductor quantum dot dispersion liquid, a solution drying step of drying a ligand solution, a washing step of washing the semiconductor quantum dot assembly on a substrate, and the like.

According to the method of producing a semiconductor film of the invention, in the semiconductor quantum dot assembly forming step, an assembly of semiconductor quantum dots is formed on a substrate by applying a semiconductor quantum dot dispersion liquid on a substrate. At this time, since the semiconductor quantum dots are dispersed in a first solvent by means of a first ligand having a longer molecular chain than a second ligand, the semiconductor quantum dots do not easily form an aggregated bulk form. Therefore, as the semiconductor quantum dot dispersion liquid is applied on a substrate, the assembly of semiconductor quantum dots can be configured such that the semiconductor quantum dots are individually arranged.

Next, a solution of a particular ligand is applied to the assembly of the semiconductor quantum dots in the ligand exchange step, and thereby ligand exchange between the first ligand coordinated to the semiconductor quantum dots and the second ligand (particular ligand) having a shorter molecular chain length than the first ligand is achieved. The particular ligand has an amino group in the molecule, as shown in Formulas (A) to (C). As discussed above, it is believed that an amino group has a high complex stability constant, and with regard to Formulas (A) and (B), the amino group promotes complex formation between the metal atom of the semiconductor quantum dots and —SH, —NH$_2$ or —OH represented by $X^1$ (or $X^2$). Furthermore, with regard to Formula (C), the amino group is believed to promote complex formation between the metal atom of the semiconductor quantum dots and OH of a carboxyl group. Therefore, it is speculated that since the second ligand (particular ligand) is coordinated in place of the first ligand having a longer molecular chain length than the second ligand, and forms a coordinate bond with a semiconductor quantum dot, close proximity between semiconductor quantum dots can be easily achieved. It is thought that when semiconductor quantum dots are brought into close proximity, electrical conductivity of the assembly of the semiconductor quantum dots is increased, and a semiconductor film having a high photoelectric current value can be obtained.

Furthermore, it is speculated that as the semiconductor quantum dots are linked by coordinate bonding via the particular ligand, the assembly of semiconductor quantum dots form a strong semiconductor film, and the semiconductor film is not easily peeled off from the substrate.

[Semiconductor Quantum Dot Assembly Forming Step]

In the semiconductor quantum dot assembly forming step, a semiconductor quantum dot dispersion liquid containing semiconductor quantum dots, a first ligand coordinated to the semiconductor quantum dots, and a first solvent is applied onto a substrate, and thereby an assembly of semiconductor quantum dots is formed.

The semiconductor quantum dot dispersion liquid may be applied on the substrate surface, or may be applied on another layer provided on the substrate.

Examples of the other layer provided on the substrate include an adhesive layer for enhancing the adhesion between the substrate and the assembly of semiconductor quantum dots, and a transparent conductive layer.

—Semiconductor Quantum Dot Dispersion Liquid—

The semiconductor quantum dot dispersion liquid contains semiconductor quantum dots containing a metal atom, a first ligand, and a first solvent.

The semiconductor quantum dot dispersion liquid may further contain other components as long as the effects of the invention are not impaired.

(Semiconductor Quantum Dots)

The details of the semiconductor quantum dots containing a metal atom, which are included in the semiconductor quantum dot dispersion liquid, are the same as those described previously, and preferred aspects thereof are also the same.

The content of the semiconductor quantum dots in the semiconductor quantum dot dispersion liquid is preferably from 1 mg/ml to 100 mg/ml, and more preferably from 5 mg/ml to 40 mg/ml.

When the content of the semiconductor quantum dots in the semiconductor quantum dot dispersion liquid is 1 mg/ml or more, the semiconductor quantum dot density on the substrate is increased, and a satisfactory film may be easily obtained. On the other hand, when the content of the semiconductor quantum dots is 100 mg/ml or less, the film thickness of the film obtainable when the semiconductor quantum dot dispersion liquid is applied once is not likely to become large. Therefore, ligand exchange of the first ligand coordinated to the semiconductor quantum dots in the film can be carried out satisfactorily.

(First Ligand)

The first ligand contained in the semiconductor quantum dot dispersion liquid works as a ligand coordinated to the semiconductor quantum dots, and also accomplishes the role as a dispersant that disperses the semiconductor quantum dots in the first solvent since the first ligand has a molecular structure that is likely to cause steric hindrance.

The first ligand has a longer molecular chain length than the second ligand that will be described below. Whether a molecular chain length is long or short is determined, in a case in which the molecule has a branched structure, by the length of the main chain. The ligand represented by Formula (A), the ligand represented by Formula (B), and the ligand represented by Formula (C), which are the second ligands, are inherently not easily dispersed in an organic solvent system, and do not correspond to the first ligand. Here, dispersion means a state in which there is no sedimentation of particles or cloudiness.

From the viewpoint of enhancing the dispersion of the semiconductor quantum dots, the first ligand is desirably a ligand having a main chain having at least 6 or more carbon atoms, and more desirably a ligand having a main chain having at least 10 or more carbon atoms.

Specifically, the first ligand may be any of a saturated compound or an unsaturated compound, and examples thereof include decanoic acid, lauric acid, myristic acid, palmitic acid, stearic acid, behenic acid, oleic acid, erucic acid, oleylamine, dodecylamine, dodecanethiol, 1,2-hexadecanethiol, trioctylphosphine oxide, and cetrimonium bromide.

It is preferable that the first ligand is not likely to remain in the film at the time of forming a semiconductor film.

Among the compounds described above, from the viewpoint of being not likely to remain in the semiconductor film while imparting dispersion stability to the semiconductor quantum dots, the first ligand is preferably at least one of oleic acid or oleylamine.

The content of the first ligand in the semiconductor quantum dot dispersion liquid is preferably from 10 mmol/l to 200 mmol/l relative to the total volume of the semiconductor quantum dot dispersion liquid.

(First Solvent)

The first solvent included in the semiconductor quantum dot dispersion liquid is not particularly limited; however, the first solvent is preferably a solvent which does not easily dissolve the semiconductor quantum dots, but can easily dissolve the first ligand. The first solvent is preferably an organic solvent, and specific examples include an alkane [n-hexane, n-octane or the like], benzene, and toluene.

The first solvent may be used singly, or in combination of two or more kinds thereof.

Among the solvents described above, the first solvent is preferably a solvent which is not likely to remain in the semiconductor film thus formed. If a solvent having a relatively lower boiling point is used, when a semiconductor film is finally obtained, the content of the residual organic materials therein can be suppressed.

Furthermore, a solvent having high wettability to the substrate is definitely preferable. For example, in the case of applying the semiconductor quantum dot dispersion liquid on a glass substrate, an alkane such as hexane or octane is more preferred.

The content of the first solvent in the semiconductor quantum dot dispersion liquid is preferably from 90% by mass to 98% by mass relative to the total mass of the semiconductor quantum dot dispersion liquid.

—Substrate—

The semiconductor quantum dot dispersion liquid is applied onto a substrate.

There are no particular limitations on the shape, structure, size and the like of the substrate, and the substrate may be appropriately selected according to the purpose. The structure of the substrate may be a single layer structure or may be a laminated structure. For example, substrates formed from inorganic materials such as glass and YSZ (yttria-stabilized zirconia), resins, resin composite materials, and the like can be used. Among them, a substrate formed from a resin or a resin composite material is preferred from the viewpoint of being lightweight and flexible.

Examples of the resin include synthetic resins such as polybutylene terephthalate, polyethylene terephthalate, polyethylene naphthalate, polybutylene naphthalate, polystyrene, polycarbonate, polysulfone, polyether sulfone, polyarylate, allyl diglycol carbonate, polyamide, polyimide, polyamideimide, polyether imide, polybenzazole, polyphenylene sulfide, polycycloolefin, norbornene resins, fluororesins such as polychlorotrifluoroethylene, liquid crystalline polymers, acrylic resins, epoxy resins, silicone resins, ionomer resins, cyanate resins, crosslinked fumaric acid diesters, cyclic polyolefins, aromatic ethers, maleimide olefins, cellulose, and episulfide compounds.

Examples of a composite material of an inorganic material and a resin include composite plastic materials of resins and the following inorganic materials. That is, examples thereof include composite plastic materials of resins and silicon oxide particles, composite plastic materials of resins and metal nanoparticles, composite plastic materials of resins and inorganic oxide nanoparticles, composite plastic materials of resins and inorganic nitride nanoparticles, composite plastic materials of resins and carbon fibers, composite plastic materials of resins and carbon nanotubes, composite plastic materials of resins and glass flakes, composite plastic materials of resins and glass fibers, composite plastic materials of resins and glass beads, composite plastic materials of resins and clay minerals, composite plastic materials of resins and particles having a mica-derived crystal structure, laminated plastic materials having at least one joint interface between a resin and a thin glass plate, and composite materials having at least one or more joint interface by alternately laminating inorganic layers and organic layers and having barrier performance.

A stainless steel substrate, a multilayer metal substrate obtained by laminating stainless steel and a metal of another kind, an aluminum substrate, an oxide coating-clad aluminum substrate having the insulation properties of the surface enhanced by subjecting an aluminum substrate to a surface oxidation treatment (for example, anodization treatment), and the like may also be used.

It is preferable that the substrate formed from a resin or a resin composite material (a resin substrate or a resin composite material substrate) is excellent in heat resistance, dimensional stability, solvent resistance, electrical insulating properties, processability, low gas permeability, low hygroscopicity, and the like. The resin substrate and the resin composite material substrate may include a gas barrier layer for preventing the penetration of moisture, oxygen and the like, an undercoat layer for enhancing flatness of the resin substrate or adhesiveness to a lower electrode, or the like.

Furthermore, a lower electrode, an insulating film or the like may also be provided on the substrate, and in that case, the semiconductor quantum dot dispersion liquid is applied on the lower electrode, insulating film or the like over the substrate.

The thickness of the substrate is not particularly limited, but the thickness is preferably from 50 μm to 1000 μm, and more preferably from 50 μm to 500 μm. When the thickness of the substrate is 50 μm or more, flatness of the substrate itself is enhanced, and when the thickness of the substrate is 1000 μm or less, flexibility of the substrate itself is enhanced so that it becomes easier to use the semiconductor film as a flexible semiconductor device.

The technique of applying the semiconductor quantum dot dispersion liquid on a substrate is not particularly limited, and examples thereof include a method of coating the semiconductor quantum dot dispersion liquid on the substrate, and a method of immersing the substrate in the semiconductor quantum dot dispersion liquid.

Regarding the method of coating the semiconductor quantum dot dispersion liquid on the substrate, more specifically, liquid phase methods such as a spin coating method, a dipping method, an inkjet method, a dispenser method, a screen printing method, a relief printing method, an intaglio printing method, and a spray coating method can be used.

Particularly, when an inkjet method, a dispenser method, a screen printing method, a relief printing method, and intaglio printing method are used, a coating film can be formed at any position on the substrate, and since a patterning process after film formation is unnecessary, the process cost can be reduced.

[Ligand Exchange Step]

In the ligand exchange step, a solution containing a second solvent and a second ligand which has a shorter molecular chain length than the first ligand and is at least one selected from a ligand represented by Formula (A), a ligand represented by Formula (B) and a ligand represented by Formula (C), is applied to the assembly of semiconductor quantum dots formed on the substrate by the semiconductor quantum dot assembly forming step, and the first ligand coordinated to the semiconductor quantum dots is exchanged with the second ligand (particular ligand) contained in the ligand solution.

—Ligand Solution—

The ligand solution contains at least a second ligand (particular ligand) and a second solvent.

The ligand solution may further include other components as long as the effects of the invention are not impaired.

(Second Ligand)

The second ligand is the particular ligand described above, and the molecular chain length thereof is shorter than that of the first ligand. The technique of determining whether the molecular chain length of a ligand is long or short is as described in the explanation on the first ligand.

The details of the particular ligand are also as described above.

In a case in which an alcohol is used as the second solvent included in the ligand solution, it is preferable that the particular ligand has a hydroxyl group (OH) in the molecule. When the particular ligand has a hydroxyl group in the molecular structure, miscibility with an alcohol can be increased. Furthermore, when ligand exchange of the semiconductor quantum dots is carried out using a ligand solution containing the particular ligand having a hydroxyl group, if an alcohol is used as the second solvent, the ligand exchange can be carried out efficiently.

The content of the particular ligand in the ligand solution is preferably from 5 mmol/l to 200 mmol/1, and more preferably from 10 mmol, to 100 mmol/1, relative to the total volume of the ligand solution.

(Second Solvent)

The second solvent included in the ligand solution is not particularly limited; however, a solvent which can easily dissolve the particular ligand is preferable.

Such a solvent is preferably an organic solvent having a high dielectric constant, and examples thereof include ethanol, acetone, methanol, acetonitrile, dimethylformamide, dimethyl sulfoxide, butanol, and propanol.

The second solvent may be used singly, or a mixed solvent including two or more kinds thereof in mixture may also be used.

Among the solvents described above, the second solvent is preferably a solvent which is not likely to remain in the semiconductor film thus formed. From the viewpoint of being easily dried and easily removed by washing, an alcohol having a low boiling point or an alkane is preferred, and methanol, ethanol, n-hexane, or n-octane is more preferred.

The second solvent is preferably a solvent which is not miscible with the first solvent, and for example when an alkane such as hexane or octane is used as the first solvent, it is preferable to use a polar solvent such as methanol or acetone as the second solvent.

The content of the second solvent in the ligand solution is the balance obtained after subtracting the content of the particular ligand from the total mass of the ligand solution.

The method of applying the ligand solution to the assembly of semiconductor quantum dots is the same as the technique of applying the semiconductor quantum dot dispersion liquid onto a substrate, and preferred aspects thereof are also the same.

The semiconductor quantum dot assembly forming step and the ligand exchange step may be carried out repeatedly. When the semiconductor quantum dot assembly forming step and the ligand exchange step are carried out repeatedly, the electrical conductivity of the semiconductor film containing the assembly of the semiconductor quantum dots to which the particular ligand is coordinated is increased, and the thickness of the semiconductor film can be increased.

Regarding the repetition of the semiconductor quantum dot assembly forming step and the ligand exchange step, the respective steps may be repeated separately and independently; however, it is preferable to repeat a cycle of performing the semiconductor quantum dot assembly forming step and then performing the ligand exchange step. When a set of the semiconductor quantum dot assembly forming step and the ligand exchange step is repeated, unevenness of the ligand exchange may be suppressed easily.

In a case in which the semiconductor quantum dot assembly forming step and the ligand exchange step are carried out repeatedly, it is preferable to carry out film drying sufficiently after each cycle.

As the exchange ratio to the particular ligand is higher in the ligand exchange of the semiconductor quantum dot assembly, the photoelectric current value of the semiconductor film is expected to increase.

It is sufficient if the ligand exchange between the first ligand and the second ligand (particular ligand) of the semiconductor quantum dots is carried out in at least a portion of the semiconductor quantum dot assembly, and it is not necessarily the case that 100% (by number) of the first ligand is replaced by the particular ligand.

(Washing Step)

The method of producing a semiconductor film of the invention may include a washing step of washing the semiconductor quantum dot assembly on the substrate.

As the method includes a washing step, any ligand that is present in excess and any ligand that has been detached from the semiconductor quantum dots can be removed. Furthermore, any residual solvent and other impurities can be removed. Washing of the semiconductor quantum dot assembly may be carried out by pouring at least one of the first solvent or the second solvent on the assembly of semiconductor quantum dots, or a substrate having the semiconductor quantum dot assembly or a semiconductor film formed thereon may be immersed in at least one of the first solvent or the second solvent.

Washing by the washing step may be carried out after the semiconductor quantum dot assembly forming step, or may be carried out after the ligand exchange step. The washing may also be carried out after the repetition of the set of the semiconductor quantum dot assembly forming step and the ligand exchange step.

(Drying Step)

The method of producing a semiconductor film of the invention may include a drying step.

The drying step may be a dispersion liquid drying step of drying the solvent remaining in the semiconductor quantum dot assembly after the semiconductor quantum dot assembly forming step, or may be a solution drying step of drying the ligand solution after the ligand exchange step. Furthermore, the drying step may also be a comprehensive step that is carried out after repetition of the set of the semiconductor quantum dot assembly forming step and the ligand exchange step.

When the respective steps described above are carried out, a semiconductor film is produced on a substrate.

The semiconductor film thus obtained has high electrical conductivity because the semiconductor quantum dots are linked by a particular ligand that is shorter than the conventional ligands, and a high photoelectric current value can be obtained. Also, since the particular ligand has a high complex stability constant, the semiconductor film of the invention constituted by semiconductor quantum dots and a particular ligand has stabilized coordinate bonding, and has excellent strength. Thus, flaking of the semiconductor film is also suppressed.

<Electronic Device>

The use of the semiconductor film of the invention is not limited; however, since the semiconductor film of the invention has photoelectric conversion characteristics and is not easily detached, the semiconductor film can be suitably applied to various electronic devices having semiconductor films or photoelectric conversion films.

Specifically, the semiconductor film of the invention can be suitably applied to the photoelectric conversion films of solar cells, light-emitting diodes (LEDs), semiconductor layers (active layers) of thin film transistors, photoelectric conversion films of indirect type radiation image pickup apparatuses, photodetectors for the visible-infrared regions, and the like.

<Solar Cell>

A solar cell is explained as an example of an electronic device including the semiconductor film of the invention, or a semiconductor film produced by the method of producing a semiconductor film of the invention.

For example, a p-n junction type solar cell can be produced using a semiconductor film device having a p-n junction, which includes a p-type semiconductor layer including the semiconductor film of the invention and an n-type semiconductor layer.

A more specific embodiment of the p-n junction type solar cell may be, for example, a form in which a p-type semiconductor layer and an n-type semiconductor layer are provided adjacently on a transparent conductive film formed on a transparent substrate, and a metal electrode is formed on the p-type semiconductor layer and the n-type semiconductor layer.

An example of the p-n junction type solar cell is described using FIG. 1.

FIG. 1 shows a schematic cross-sectional diagram of a p-n junction type solar cell 100 related to an embodiment of the invention. The p-n junction type solar cell 100 is configured to include a transparent substrate 10; a transparent conductive film 12 provided on the transparent substrate 10; a p-type semiconductor layer 14 composed of the semiconductor film of the invention on the transparent conductive film 12; an n-type semiconductor layer 16 on the p-type semiconductor layer 14; and a metal electrode 18 provided on the n-type semiconductor layer 16, all of which are laminated.

As the p-type semiconductor layer 14 and the n-type semiconductor layer 16 are laminated adjacently, the p-n junction type solar cell can be obtained.

Regarding the transparent substrate 10, the same material as that of the substrate used in the method of producing a semiconductor film of the invention can be used as long as the material is transparent. Specific examples include a glass substrate and a resin substrate. In this invention, examples of the transparent conductive film 12 include films composed of $In_2O_3$:Sn (ITO), $SnO_2$:Sb, $SnO_2$:F, ZnO:Al, ZnO:F, and $CdSnO_4$.

For the p-type semiconductor layer 14, the semiconductor film of the invention is used as described above.

Regarding the n-type semiconductor layer 16, a metal oxide is preferred. Specific examples include oxides of metals include at least one of Ti, Zn, Sn, or In, and more specific examples include $TiO_2$, ZnO, $SnO_2$, and IGZO. It is preferable that the n-type semiconductor layer is formed by a wet method (also called a liquid phase method), similarly to the p-type semiconductor layer, from the viewpoint of the production cost.

Regarding the metal electrode 18, Pt, Al, Cu, Ti, Ni, and the like can be used.

EXAMPLES

Hereinafter, the invention is explained by way of Examples, but the invention is not intended to be limited to these Examples.

<Production of Semiconductor Film Device>

[Preparation of Semiconductor Quantum Dot Dispersion Liquid 1]

First, a PbS particle dispersion liquid in which PbS particles were dispersed in toluene was prepared. For the PbS particle dispersion liquid, PbS CORE EVIDOT (nominal particle diameter 3.3 nm, 20 mg/ml, solvent: toluene) manufactured by Evident Technologies, Inc. was used.

Subsequently, 2 ml of the PbS particle dispersion liquid was introduced into a centrifuge tube, 38 μl of oleic acid was added thereto, and then 20 ml of toluene was added thereto to decrease the concentration of the dispersion liquid. Thereafter, the PbS particle dispersion liquid was subjected to ultrasonic dispersion, and the PbS particle dispersion liquid was thoroughly stirred. Subsequently, 40 ml of ethanol was added to the PbS particle dispersion liquid, and the mixture was further subjected to ultrasonic dispersion and to centrifugation under the conditions of 10,000 rpm, 10 minutes, and 3° C. The supernatant in the centrifuge tube was discarded, subsequently 20 ml of octane was added to the centrifuge tube, and the mixture was subjected to ultrasonic dispersion. Precipitated quantum dots were thereby thoroughly dispersed in the octane solvent. The dispersion thus obtained was subjected to concentration of the solution using a rotary evaporator (35 hpa, 40° C.). As a result, about 4 ml of a semiconductor quantum dot dispersion liquid 1 (octane solvent) having a concentration of approximately 10 mg/ml was obtained.

The average particle diameter of the PbS particles included in the semiconductor quantum dot dispersion liquid 1 was 3 nm.

Meanwhile, the average particle diameter of the semiconductor quantum dots was calculated as the average of ten semiconductor quantum dots, by an observation of photographs obtained by a TEM (transmission electron microscope) measurement. For the measurement apparatus, a TITAN 80-300 manufactured by Field Emission, Inc. was used.

[Preparation of Semiconductor Quantum Dot Dispersion Liquid 2]

First, InP particles were synthesized, and an octane dispersion liquid of InP particles to which oleylamine was coordinated was prepared.

—Preparation of Octane Dispersion Liquid of Oleylamine-Modified InP Particles—

In a glove box, 30 ml of 1-octadecene, 1.81 ml of oleylamine, 0.60 g of anhydrous indium chloride, 0.49 ml of trisdimethylaminophosphine, and a magnetic stirrer were introduced into a three-necked round bottom flask in a $N_2$ gas atmosphere. Subsequently, the three-necked round bottom flask was taken out from the glove box in a state of being sealed with a stopper having a three-way valve, and the flask was placed in a magnetic stirrer-attached aluminum block thermostat bath. Thereafter, the three-way valve was operated, and the flask was purged with $N_2$ gas. While the mixture was vigorously stirred with the magnetic stirrer, heating of the aluminum block thermostat bath was started. The temperature of the aluminum block thermostat bath was increased up to 150° C. for about 30 minutes, and the temperature was maintained for 5 hours. Thereafter, heating was stopped, and the three-necked round bottom flask was cooled to room temperature using a blower fan.

The product was taken out from the three-necked round bottom flask, and unreacted materials and side products were removed by centrifugation using a centrifuge. The product (InP particles) was purified using ultra-dehydrated toluene as a good solvent and using dehydrated ethanol as a poor solvent. Specifically, a treatment of dissolving the product in the good solvent, redispersing the InP particle solution in the poor solvent, and centrifuging the InP particle dispersion liquid thus obtained, was repeated. For the redispersion, an ultrasonic cleaner was used. After the centrifugation of the InP particle dispersion liquid was repeated, the dehydrated ethanol remaining in the InP particle dispersion liquid was removed by distilling under reduced pressure using a rotary evaporator. Finally, the InP particles thus extracted were dispersed in octane, and thus an octane dispersion liquid having an oleylamine-modified InP particle concentration of 1 mg/ml was obtained. This was designated as a semiconductor quantum dot dispersion liquid 2.

The InP particles thus obtained were observed by TEM, and the particles were particles having an average particle diameter of about 4 nm.

[Preparation of Semiconductor Quantum Dot Dispersion Liquid 3]

In a three-necked flask, 30 ml of 1-octadecene, 6.32 mmol of lead(II) oxide, and 21.2 mmol of oleic acid were respectively weighed and mixed. The mixture was stirred with a magnetic stirrer at 300 rpm using an aluminum block hot plate stirrer. During the stirring of the mixture, degassing and dehydration were carried out in a vacuum at 120° C. for 1 hour. Subsequently, the three-necked flask was cooled to room temperature using a cooling fan, and purging with nitrogen gas was carried out. Subsequently, a solution containing 2.57 mmol of hexamethyldisilazane and 5 ml of 1-octadecene was injected into the three-necked flask using a syringe (injected by sticking the syringe needle into the septum cap). Thereafter, the three-necked flask was heated to 120° C. for 40 minutes and maintained for 1 minute, and then the three-necked flask was cooled to room temperature with a cooling fan. Unnecessary materials were removed from the product thus obtained, using a centrifuge, and only the PbS particles were extracted and dispersed in octane. When the unnecessary materials were removed from the product, toluene was used as a good solvent, and dehydrated ethanol was used as a poor solvent.

As a result of an observation using a STEM (scanning transmission electron microscope), it was found that the average particle diameter of the PbS thus obtained was 5 nm.

This octane dispersion liquid of PbS quantum dots was further diluted with a hexane solvent, and thereby a semiconductor quantum dot dispersion liquid 3 [mixed solvent of octane:hexane=1:9 (volume ratio)] having a concentration of approximately 10 mg/ml was obtained.

[Preparation of Ligand Solution]

A ligand solution having a concentration of 0.1 mol/l was prepared by apportioning 1 mmol of the ligand indicated in the column "Compound name" in the column "Ligand" of Table 1 and dissolving the ligand in 10 ml of methanol. In order to accelerate dissolution of the ligand in the ligand solution, the ligand solution was irradiated with ultrasonic waves so that the ligand dissolved as much as possible and there was no residue.

[Substrate]

Figure 2:
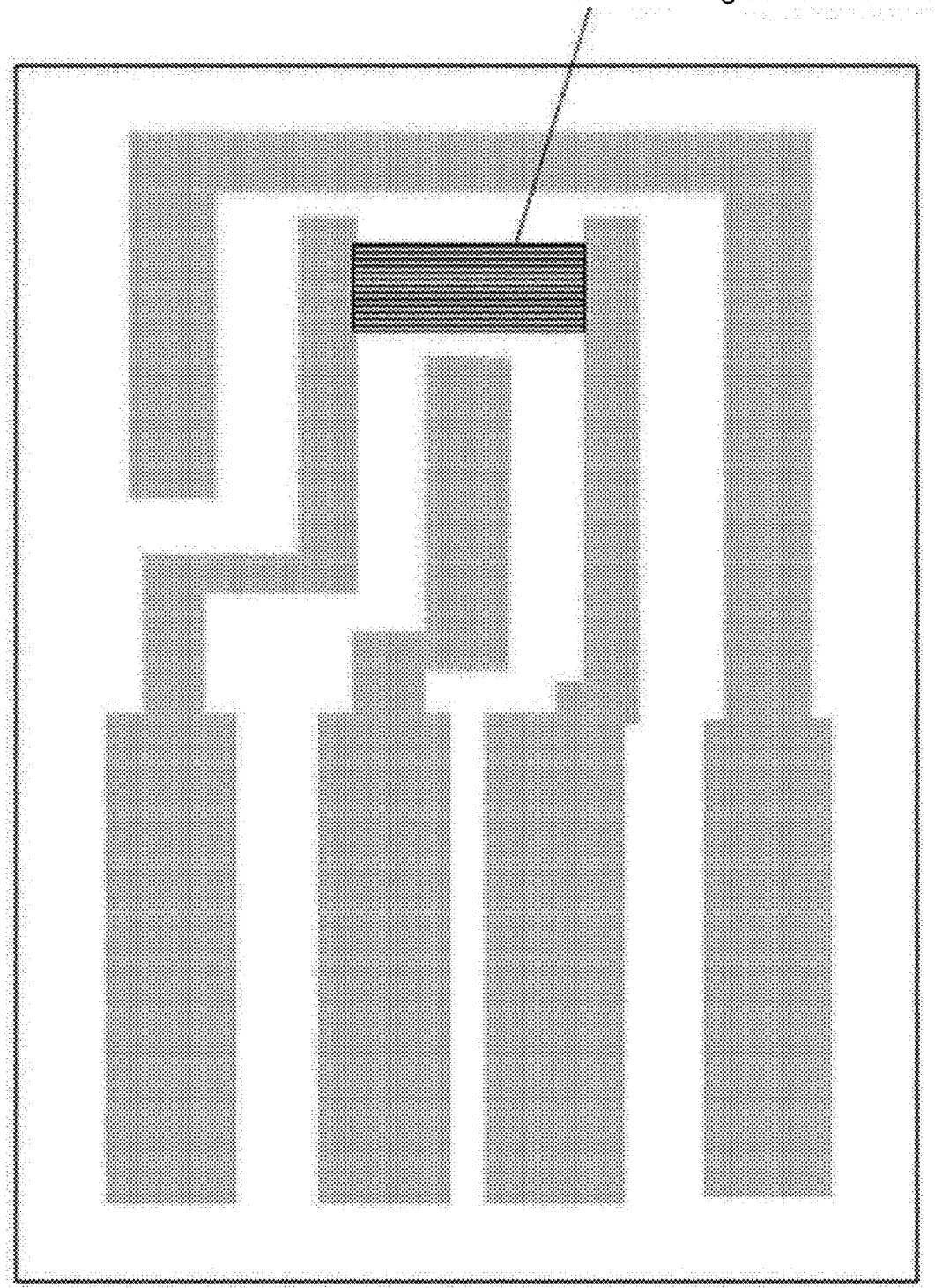
FIG. 2 is an outline diagram illustrating a substrate with interdigitated electrodes used in the Examples.

Regarding the substrate, a substrate having 65 pairs of interdigitated platinum electrodes illustrated in FIG. 2 on a quartz glass plate was prepared. For the interdigitated platinum electrodes, interdigitated electrodes manufactured by Bioanalytical Systems, Inc. (product No. 012126, electrode spacing: 5 μm) were used.

[Production of Semiconductor Film]

(1) Semiconductor Quantum Dot Assembly Forming Step

The semiconductor quantum dot dispersion liquid 1 or the semiconductor quantum dot dispersion liquid 2 thus prepared was dropped on a substrate, and then the dispersion liquid was spin coated at 2500 rpm. Thus, a semiconductor quantum dot assembly film was obtained.

(2) Ligand Exchange Step

Furthermore, a methanol solution of the ligand indicated in Table 1 (ligand solution) was dropped on the semiconductor quantum dot assembly film, and then the methanol solution was spin coated at 2500 rpm. Thus, a semiconductor film was obtained.

(3) Washing Step 1

Subsequently, only methanol, which was the solvent of the ligand solution, was dropped on the semiconductor film, and the solvent was spin coated.

(4) Washing Step 2

Furthermore, only an octane solvent was dropped on the semiconductor film after the washing by the washing step 1, and the octane solvent was spin coated.

The series of steps (1) to (4) were repeated for 15 cycles, and thereby a semiconductor film having a thickness of 100 nm, which was formed from an assembly of PbS quantum dots and had been subjected to ligand exchange, was obtained.

A semiconductor film device having a semiconductor film on a substrate was produced as described above.

The combinations of the semiconductor quantum dot dispersion liquids and the ligand solutions in Examples and Comparative Examples are as indicated in Table 1. In Table 1, "PbS" in the column "Kind" of the column "Semiconductor quantum dot" means that the semiconductor quantum dot dispersion liquid 1 was used, and "InP" means that the semiconductor quantum dot dispersion liquid 2 was used.

Furthermore, the kind of the ligand included in the ligand solution is the ligand indicated in the column "Compound name" of the column "Ligand" of Table 1.

Meanwhile. "A" in the columns "Ligand", "Formula" and "Kind" means that the ligand is represented by Formula (A), "B" means that the ligand is represented by Formula (B), and "C" means that the ligand is represented by Formula (C). Any ligands that cannot be represented by Formulas (A), (B), and (C) are indicated by symbol "-". Also, "Number of A" indicates the number of atoms of $A^1$, $A^2$, or $A^3$, and "Number of B" represents the number of atoms of $B^1$ or $B^2$.

Furthermore, the ligand used in Comparative Example 4 is potassium bromide (KBr), and the ligand used in Comparative Example 5 is cetyltrimethylammonium bromide $[(CH_3(CH_2)_{15}N(CH_3)_3)^+, Br^-]$.

<Evaluation of Semiconductor Film>

The semiconductor films of the semiconductor film devices thus obtained were subjected to various evaluations.

1. Electrical Conductivity

An evaluation of the electrical conductivity of a semiconductor film was carried out by employing a semiconductor parameter analyzer for a semiconductor film device thus produced.

First, the voltage applied to the electrodes was scanned between −5 V and 5 V in a state that no light was irradiated to a semiconductor film device, and thus the I-V characteristics in a dark state were obtained. The electric current value in a state of having a bias of +5 V applied thereto was employed as the value of dark current, Id.

Figure 3:
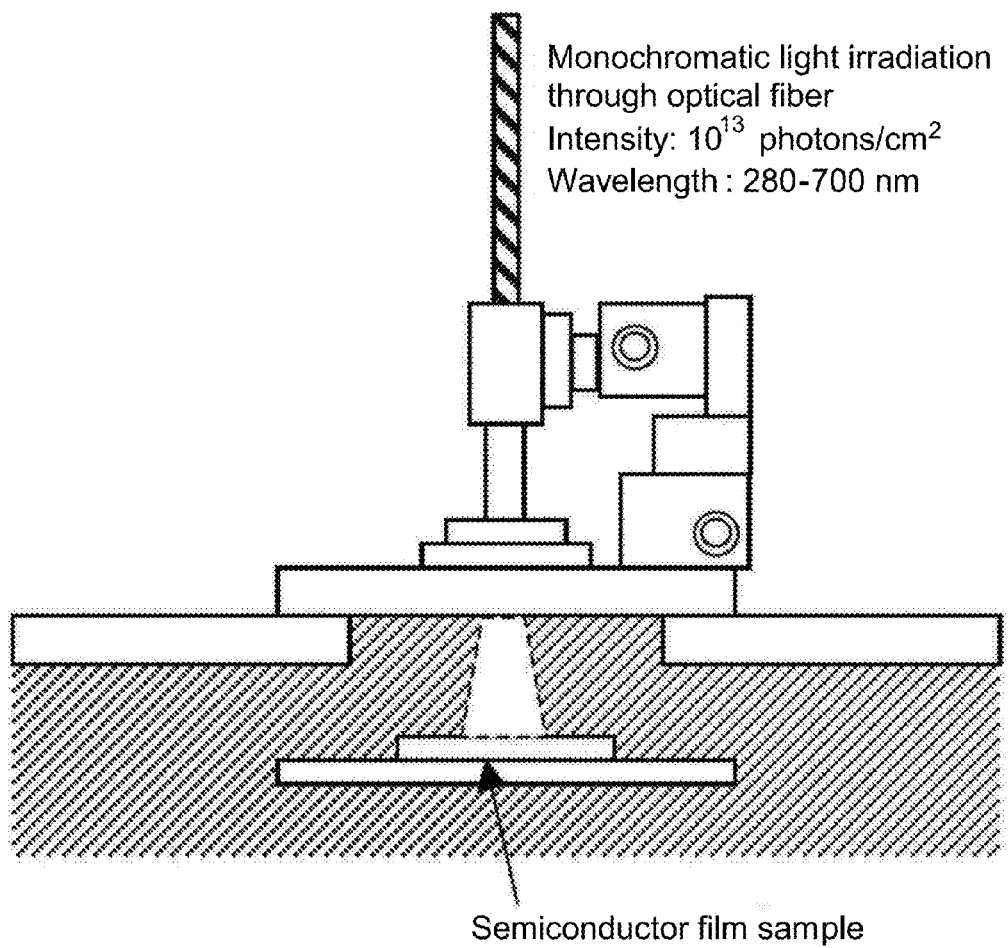
FIG. 3 is an outline diagram illustrating the method of irradiating monochromatic light to a semiconductor film produced in the Examples.
Figure 4:
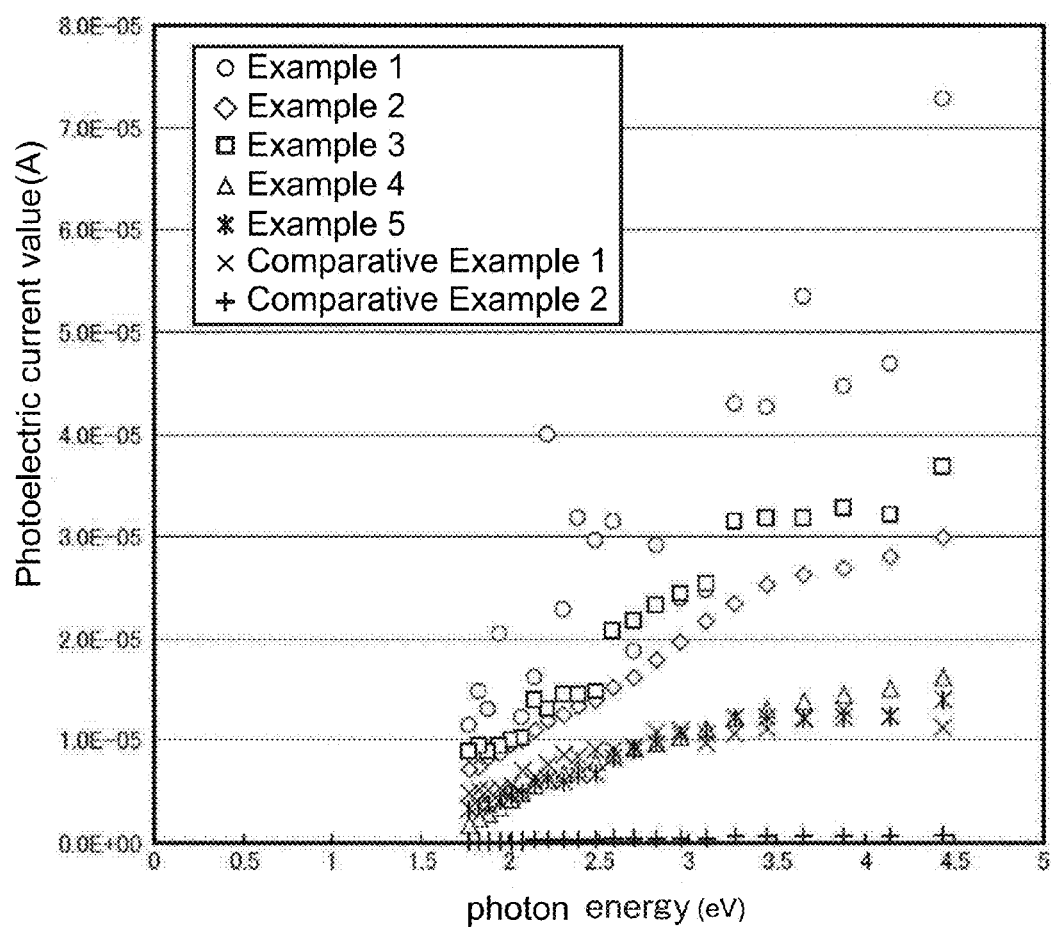
FIG. 4 is a diagram illustrating the relationship between the photoelectric current value and the irradiation energy.

Next, the photoelectric current value in a state of having monochromatic light (irradiation intensity: $10^{13}$ photons) irradiated to the semiconductor film device was evaluated. The irradiation of monochromatic light to the semiconductor film device was carried out using the apparatus illustrated in FIG. 3. The wavelength of the monochromatic light was varied systematically between 280 nm and 700 nm. The increment of the electric current from the dark current in the case of irradiating light having a wavelength of 280 nm was designated as the photoelectric current value, Ip.

The evaluation results are presented in Table 1.

2. Film Flaking from Substrate

For the semiconductor film devices of the Examples and Comparative Examples, flaking of the semiconductor films was evaluated by visual inspection. The presence or absence of film flaking is indicated in Table 1.

3. Complex Stability ($\log \beta_1$)

The complex stability constants ($\log \beta_1$) of the ligands carried by the semiconductor films of the Examples and Comparative Examples were obtained by retrieving the Sc-Database ver. 5.85 (Academic Software) (2010).

Also, the complex stability constants ($\log \beta_1$) of those ligands that are not listed in the Sc-Database were calculated using the above-described formula (b), from the concentration of the semiconductor quantum dots (PbS particles or InP particles) in the semiconductor quantum dot dispersion liquid and the concentration of the ligand in the ligand solution.

The results are presented in Table 1.

Meanwhile, those complex stability constants that are not described in the Sc-Database ver. 5.85 and could not be easily calculated are indicated by symbol "-".

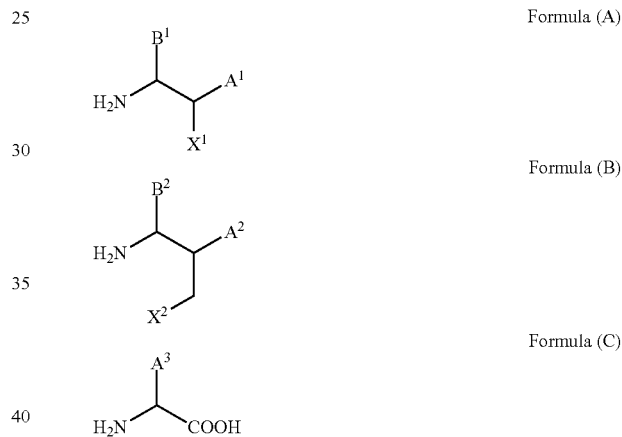

TABLE 1

| | | Ligand | | | | | |
|---|---|---|---|---|---|---|---|
| | | | | Formula | | | |
| | Compound name | Kind | $X^1, X^2$ | $A^1, A^2, A^3$ | Number of A | $B^1, B^2$ | Number of B |
| Example 1 | 2-Aminoethane-1-thiol | A | SH | H | 1 | H | 1 |
| Example 2 | 2-Aminoethanol | A | OH | H | 1 | H | 1 |
| Example 3 | 3-Amino-1-propanol | B | OH | H | 1 | H | 1 |
| Example 4 | L-homoserine | B | OH | H | 1 | COOH | 4 |
| Example 5 | L-cysteine | A | SH | H | 1 | COOH | 4 |
| Example 6 | 1-Amino-2-butanol | A | OH | $CH_2CH_2$ | 7 | H | 1 |
| Example 7 | 1-Amino-2-pentanol | A | OH | $CH_2CH_2CH_3$ | 10 | H | 1 |
| Example 8 | 2,3-Diaminopropionic acid | A | $NH_2$ | H | 1 | COOH | 4 |
| Example 9 | Aminohydroxyacetic acid | C | — | OH | 1 | — | — |
| Comparative Example 1 | Ethanedithiol | — | — | — | — | — | — |
| Comparative Example 2 | Ethylenediamine | A | $NH_2$ | H | 1 | H | 1 |
| Comparative Example 3 | Oxalic acid | — | — | — | — | — | — |
| Comparative Example 4 | KBr | — | — | — | — | — | — |
| Comparative Example 5 | CTAB | — | — | — | — | — | — |

TABLE 1-continued

| | | | | | | | |
|---|---|---|---|---|---|---|---|
| Comparative Example 6 | Trithiocyanuric acid | — | — | — | — | — | — |
| Comparative Example 7 | Thiazole | — | — | — | — | — | — |
| Comparative Example 8 | Imidazole | — | — | — | — | — | — |
| Comparative Example 9 | 1-Amino-2-,5-pentanediol | A | OH | $(CH_2)_3OH$ | 11 | H | 1 |
| Example 10 | 2-Aminoethane-1-thiol | A | SH | H | 1 | H | 1 |
| Example 11 | 2-Aminoethanol | A | OH | H | 1 | H | 1 |
| Comparative Example 10 | Ethanedithiol | — | — | — | — | — | — |

| | Semiconductor quantum dot | | | | | |
|---|---|---|---|---|---|---|
| | Kind | Average particle diameter nm | Photoelectric current value Ip [A] | Dark current value Id [A] | Presence or absence of film flaking | Complex stability $\log\beta_1$ |
| Example 1 | PbS | 3 | $7.28 \times 10^{-5}$ | $2.01 \times 10^{-3}$ | Absent | 10.1 |
| Example 2 | PbS | 3 | $2.99 \times 10^{-5}$ | $1.47 \times 10^{-4}$ | Absent | 8.4 |
| Example 3 | PbS | 3 | $3.69 \times 10^{-5}$ | $1.31 \times 10^{-4}$ | Absent | — |
| Example 4 | PbS | 3 | $1.40 \times 10^{-5}$ | $6.21 \times 10^{-5}$ | Absent | — |
| Example 5 | PbS | 3 | $1.81 \times 10^{-5}$ | $6.54 \times 10^{-5}$ | Absent | 12.2 |
| Example 6 | PbS | 3 | $2.35 \times 10^{-5}$ | $1.05 \times 10^{-4}$ | Absent | — |
| Example 7 | PbS | 3 | $1.35 \times 10^{-5}$ | $6.02 \times 10^{-5}$ | Absent | — |
| Example 8 | PbS | 3 | $1.52 \times 10^{-5}$ | $7.12 \times 10^{-5}$ | Absent | — |
| Example 9 | PbS | 3 | $1.75 \times 10^{-5}$ | $8.21 \times 10^{-5}$ | Absent | — |
| Comparative Example 1 | PbS | 3 | $1.13 \times 10^{-5}$ | $5.31 \times 10^{-5}$ | Present | — |
| Comparative Example 2 | PbS | 3 | $7.33 \times 10^{-7}$ | $1.31 \times 10^{-6}$ | Absent | 5.05 |
| Comparative Example 3 | PbS | 3 | $3.63 \times 10^{-8}$ | $5.47 \times 10^{-8}$ | Absent | — |
| Comparative Example 4 | PbS | 3 | $3.49 \times 10^{-6}$ | $1.51 \times 10^{-5}$ | Absent | 1.1* |
| Comparative Example 5 | PbS | 3 | $5.44 \times 10^{-6}$ | $2.26 \times 10^{-5}$ | Absent | 1.1* |
| Comparative Example 6 | PbS | 3 | $3.50 \times 10^{-7}$ | $1.11 \times 10^{-6}$ | Present | — |
| Comparative Example 7 | PbS | 3 | $1.54 \times 10^{-7}$ | $3.53 \times 10^{-7}$ | Absent | — |
| Comparative Example 8 | PbS | 3 | $6.98 \times 10^{-6}$ | $2.30 \times 10^{-5}$ | Absent | 2.9 |
| Comparative Example 9 | PbS | 3 | $9.81 \times 10^{-6}$ | $4.82 \times 10^{-5}$ | Absent | — |
| Example 10 | InP | 4 | $5.63 \times 10^{-12}$ | $5.22 \times 10^{-12}$ | Absent | — |
| Example 11 | InP | 4 | $8.53 \times 10^{-11}$ | $5.41 \times 10^{-9}$ | Absent | — |
| Comparative Example 10 | InP | 4 | $2.24 \times 10^{-13}$ | $4.24 \times 10^{-12}$ | Absent | — |

1.1*: the value obtained in the case of considering that the ligand is only a Br atom.

As shown in Table 1, it was found that when the oleic acid ligand coordinated to the semiconductor quantum dots is subjected to ligand exchange, and the semiconductor quantum dots are linked by the ligand represented by Formula (A), Formula (B) or Formula (C), a high photoelectric current value and a high dark current value are obtained compared to a conventional semiconductor film to which ethanedithiol is coordinated (Comparative Example 1).

Furthermore, in the semiconductor film to which ethanedithiol was coordinated, significant film flaking was observed by visual inspection, while film flaking was not recognized in the semiconductor film devices of the Examples, and satisfactory roughness was realized.

Moreover, it was found that in the semiconductor film using ethylenediamine as the ligand (Comparative Example 2), the photoelectric current value and the dark current value were both lowered significantly.

As discussed above, the results shown in Table 1 suggest that when a simple primary amine or a diamine is used as the ligand, satisfactory electrical conduction characteristics cannot be obtained. This implies that there is a possibility that a simple primary amine or a diamine has a log $\beta_1$ value which is not so high, and the ligand is not sufficiently coordinated. Therefore, it is speculated that oleic acid remains as a ligand and inhibits the transport of carriers between the semiconductor quantum dots.

From the results of Example 1 to Example 3 having particularly high carrier transportation characteristics, it is understood that when $X^1$ in Formula (A) and $X^2$ in Formula (B) represent OH or SH, a high photoelectric current value is obtained, and excellent electrical conduction characteristics are obtained.

As such, it was found that when a semiconductor film in which a particular ligand is coordinated to semiconductor quantum dots is produced, a high photoelectric current and high electrical conductivity can be realized, and film flaking is also suppressed.

4. Irradiation Energy-Dependency of Photoelectric Current Value

The dependency of the photoelectric current value on the irradiation energy was evaluated by making the number of irradiated photons constant, and varying the irradiation energy in the evaluation on the photoelectric current value carried out in the evaluation of "1. Electrical Conductivity". The evaluation results are presented in Table 4.

5. Photoluminescence Spectrum of Semiconductor Quantum Dots

As can be seen from the evaluation results of the Examples and Comparative Examples shown in Table 1, when the semiconductor quantum dots are brought into close proximity to one another using a particular ligand, electrical conductivity of the semiconductor film can be increased. However, on the other hand, if the semiconductor quantum dots are excessively brought into close proximity to one another, aggregation of the semiconductor quantum dots is likely to occur. It is anticipated that the semiconductor quantum dots exhibit the nature of a bulk state as a result of aggregation.

It is preferable that a semiconductor film maintains the properties of semiconductor quantum dots while exhibiting satisfactory electrical characteristics. Particularly, when it is contemplated to apply the semiconductor film to an LED or a solar cell, if the semiconductor film does not have the properties as semiconductor quantum dots, it is difficult to obtain the absorption or emission of an intended wavelength.

This can be determined from the peak wavelength of the PL (photoluminescence) spectrum for semiconductor quantum dots having a ligand.

Thus, a PL spectrum measurement of the semiconductor films according to Examples 1 and 2 among the Examples, and Comparative Example 1 and Comparative Examples 4 to 8 among the Comparative Examples was carried out. For reference, the PL spectra of a film of PbS semiconductor quantum dots using glycolic acid as a ligand (Comparative Example 11), a film of PbS semiconductor quantum dots to which oleic acid was coordinated without ligand exchange (Comparative Example 12), and PbS in a bulk state (Comparative Example 13) were also measured.

Here, the film of Comparative Example 11 is a semiconductor film obtained in the same manner as in Example 1, using a ligand solution obtained in the same manner as in Example 1 except that the ligand was changed to glycolic acid. The film of Comparative Example 12 is a film obtained by not conducting the steps (2) and (3) among the steps (1) to (4) for the "Production of semiconductor film" in Example 1. The film of Comparative Example 12 was an insulating film that did not exhibit electrical conductivity because the semiconductor quantum dots were not brought into close proximity to one another.

PbS in a bulk state is a common Group II-VI semiconductor, and is single crystals of PbS with a size larger than 100 nm and does not provide the quantum size effect.

Figure 5:
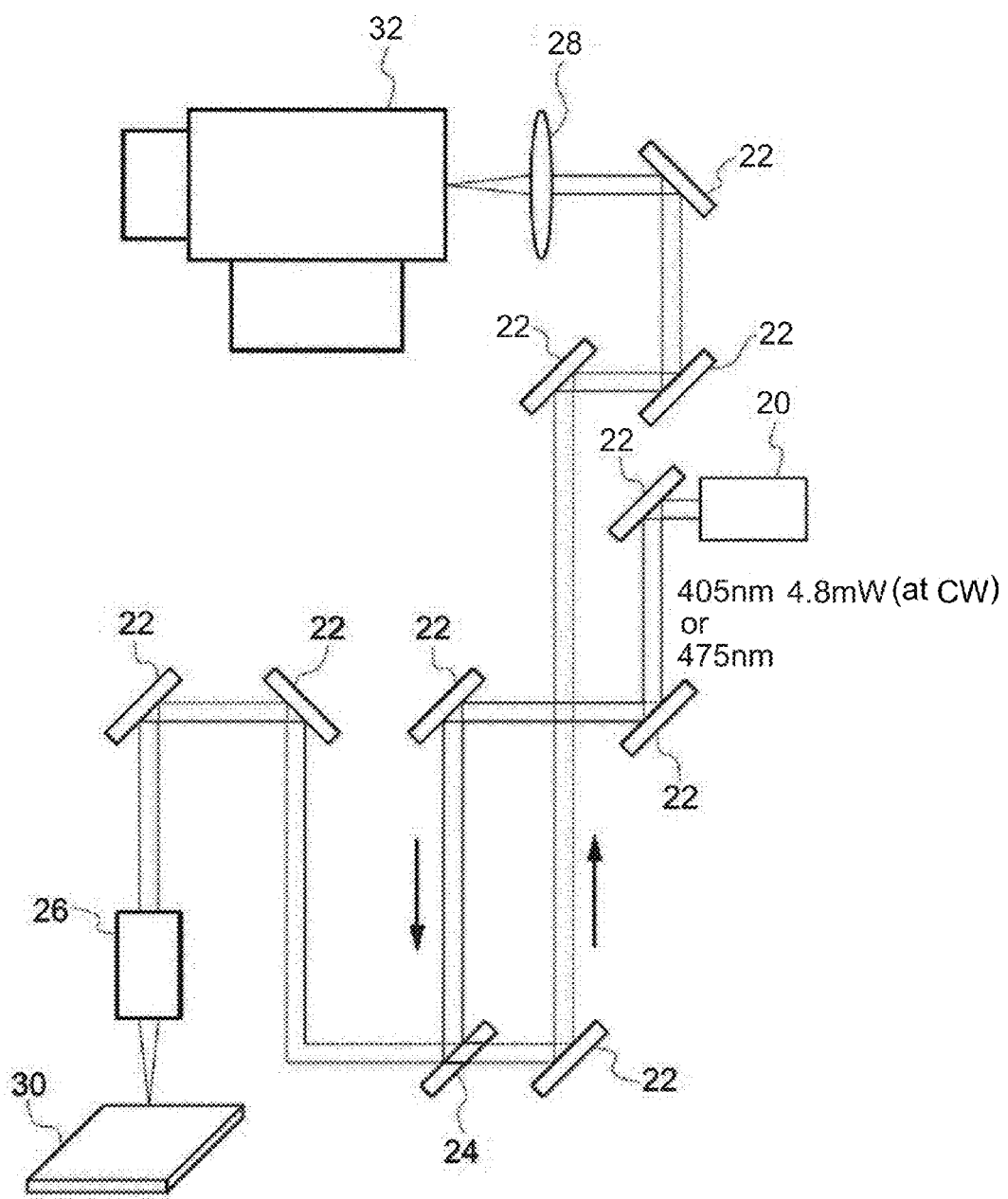
FIG. 5 is an outline diagram illustrating the configuration of an experimental system used for the photoluminescence measurement in the Examples.

The configuration of the setting of the experimental system used for the photoluminescence measurement is schematically shown in FIG. 5. This experimental apparatus essentially includes a laser irradiator 20, a total reflection mirror 22, a dichroic mirror 24, lenses 26 and 28, and a spectrometer 32, and has a configuration in which laser light emitted from the laser irradiator 20 passes the total reflection mirror 22, the dichroic mirror 24, and the lenses 26 and 28 and reaches a measurement sample (semiconductor film of the device for evaluation) 30 and the spectrometer 32.

Figure 6:
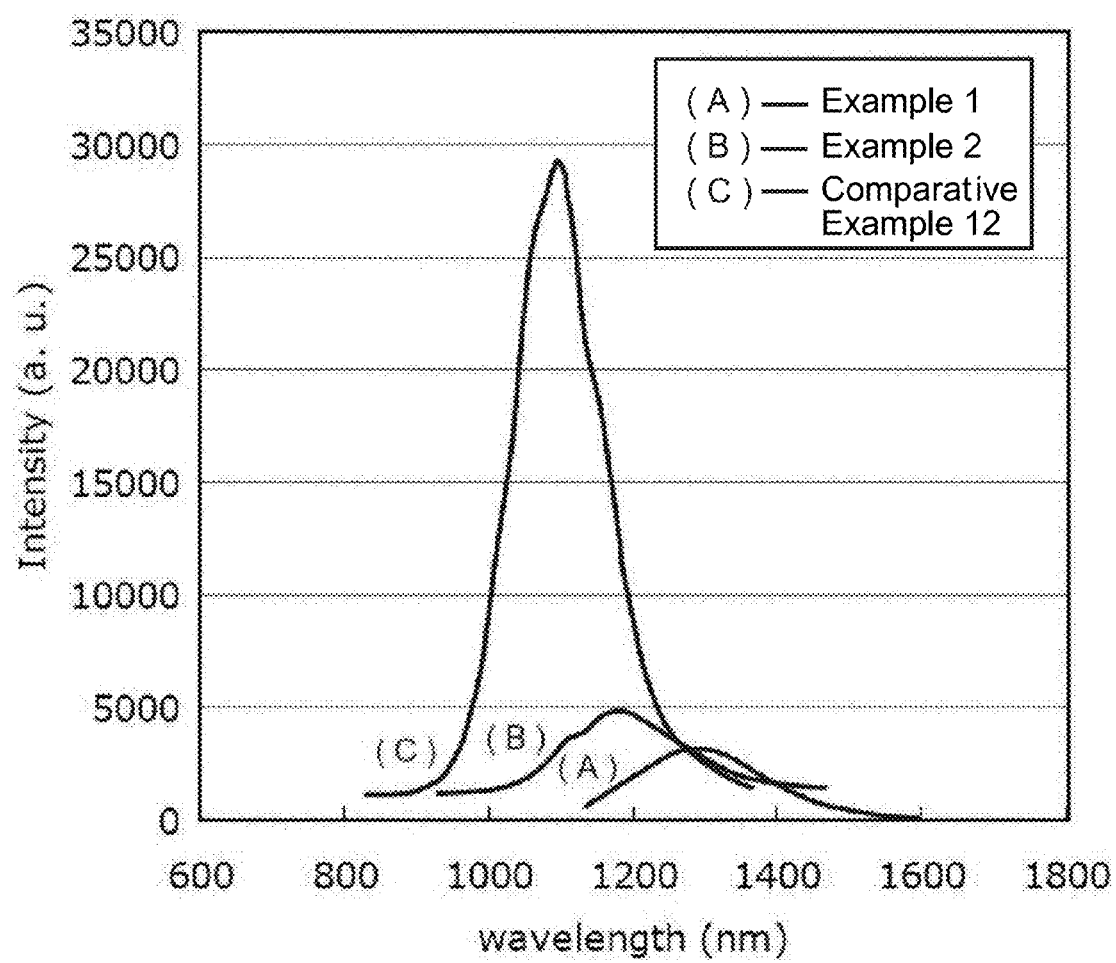
FIG. 6 is a diagram illustrating the results of photoluminescence measurement with respect to respective ligands.
Figure 7:
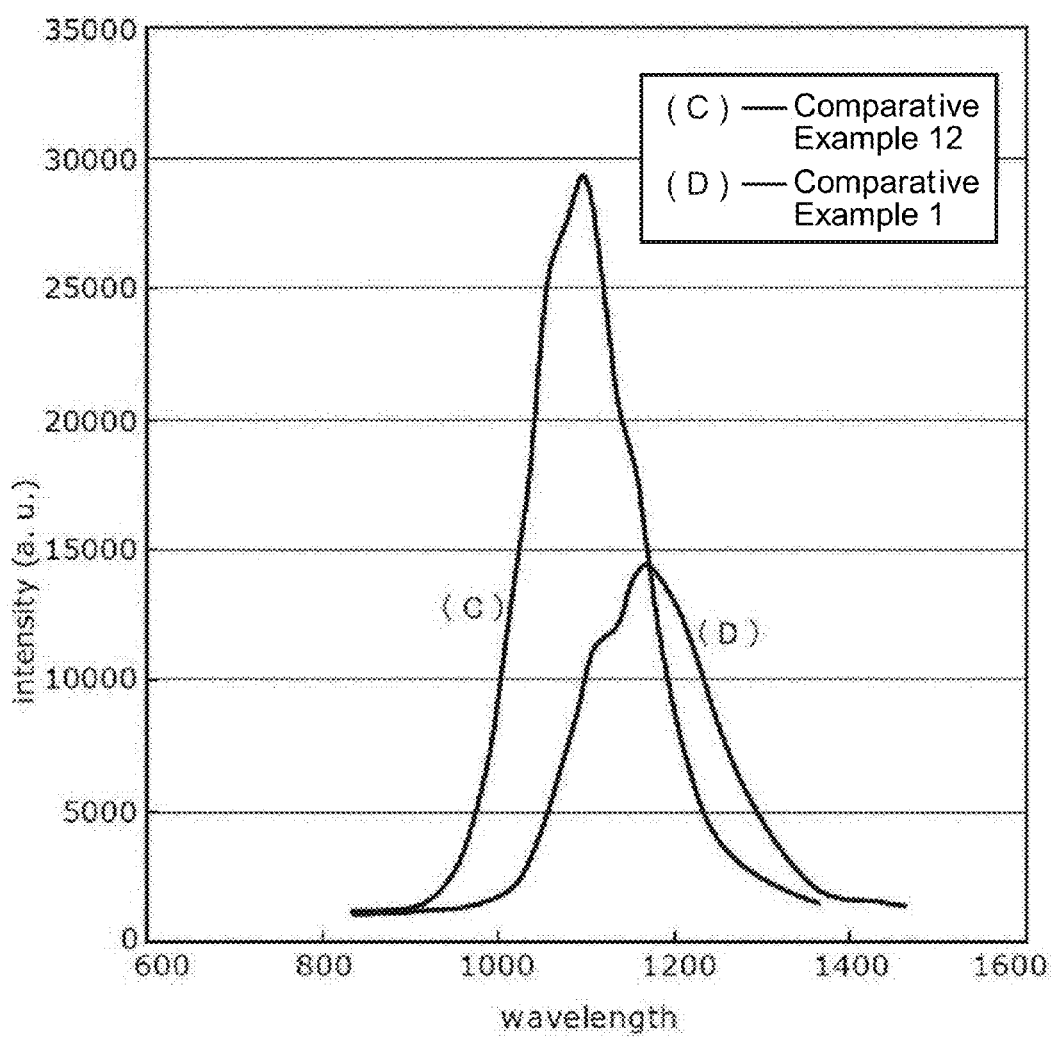
FIG. 7 is a diagram illustrating the results of photoluminescence measurement with respect to respective ligands.
Figure 8:
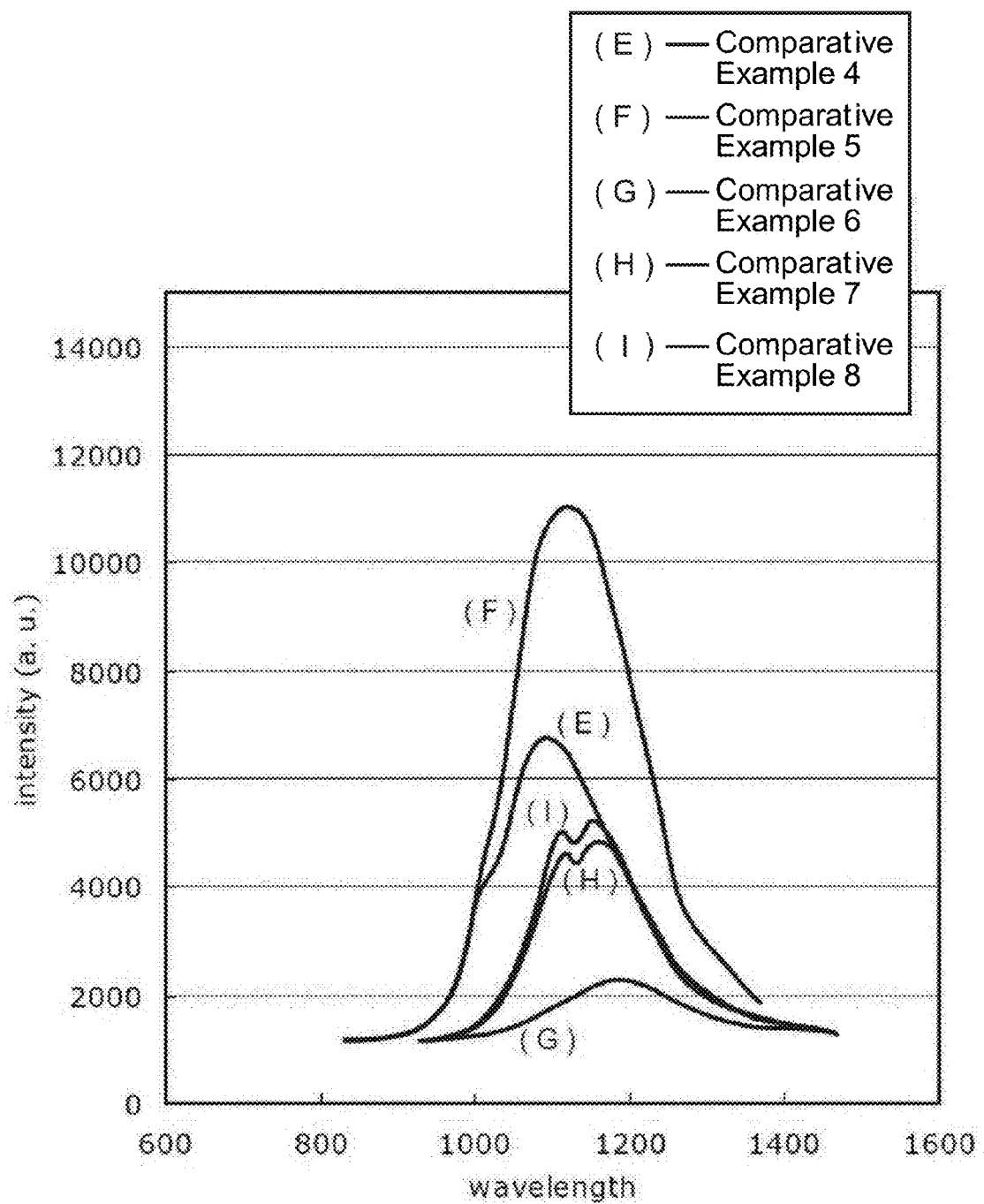
FIG. 8 is a diagram illustrating the results of photoluminescence measurement with respect to respective ligands.

FIG. 6 to FIG. 8 show the PL spectra. FIG. 6 presents the PL spectra of Example 1 (curve A), Example 2 (curve B), and Comparative Example 12 (curve C). FIG. 7 presents the PL spectra of Comparative Example 1 (curve D) and Comparative Example 12 (curve C), and FIG. 8 presents the PL spectra of Comparative Examples 4 to 8 (curve E to curve I).

Also, the peak wavelengths for the respective ligands are summarized in Table 2.

TABLE 2

| | Ligand | Peak wavelength | FIGS. 6 to 8 |
|---|---|---|---|
| Example 1 | 2-Aminoethane-1-thiol | 1290 | Curve (A) |
| Example 2 | 2-Aminoethanol | 1180 | Curve (B) |
| Comparative Example 1 | Ethanedithiol | 1169 | Curve (D) |
| Comparative Example 4 | KBr | 1192 | Curve (E) |
| Comparative Example 5 | CTAB | 1216 | Curve (F) |
| Comparative Example 6 | Trithiocyanuric acid | 1182 | Curve (G) |
| Comparative Example 7 | Thiazole | 1159 | Curve (H) |
| Comparative Example 8 | Imidazole | 1157 | Curve (I) |
| Comparative Example 11 | Glycolic acid | 1222 | None |
| Comparative Example 12 | Oleic acid (untreated) | 1097 | Curve (C) |
| Comparative Example 13 | PbS bulk | 3350 | None |

As can be seen from FIG. 6 to FIG. 8 and Table 2, the PbS semiconductor quantum dots to which oleic acid was coordinated without ligand exchange (Comparative Example 12) had a peak wavelength of about 1100 nm. On the other hand, it is understood that in the semiconductor films other than the semiconductor film to which 2-aminoethane-1-thiol is coordinated (Example 1), the peak wavelength is shifted to the longer wavelength side by about 60 nm to 120 nm.

The shift of the peak wavelength to the longer wavelength side occurred because the confining potential of the semiconductor quantum dots was decreased as a result of the semiconductor quantum dots being brought into close proximity to one another due to ligand exchange, and the band gap was substantially decreased. The decrement of the band gap is approximately 100 meV at the maximum.

On the other hand, in the case of PbS in a bulk state (Comparative Example 13), since the band gap is approximately 0.37 eV, the photoluminescence peak exists at about 3350 nm. Accordingly, it is contemplated that if the semiconductor quantum dots of a semiconductor film form an aggregate, the photoluminescence peak of the semiconductor film composed of the aggregate of semiconductor quantum dots appears at near 3350 nm.

In contrast, as can be seen from Example 1 and Example 2, it was confirmed that a semiconductor film of semiconductor quantum dots to which a particular ligand is coordinated has a shorter distance between semiconductor quantum dots and has high electrical conduction characteristics via semiconductor quantum dots, and the semiconductor film also maintains the properties as semiconductor quantum dots (band gap and the like).

Furthermore, in regard to a semiconductor film of semiconductor quantum dots to which 2-aminoethanethiol is coordinated (Example 1), it was found that the peak wavelength appears at near 1290 nm.

The photoluminescence peak of the semiconductor film of Example 1 is different from the photoluminescence peak of the bulk state and from the photoluminescence peak of normal semiconductor quantum dots, which suggests that a new energy level has been formed in which the energy level of the semiconductor quantum dots is modulated because the semiconductor quantum dots are brought into very close proximity to one another.

6. Average Particle Diameter of Semiconductor Quantum Dots

The average particle diameter of the semiconductor quantum dots was measured using a TEM apparatus. A TITAN 80-300 manufactured by Field Emission, Inc. was used as the measurement apparatus. Two kinds of samples were prepared. One was a sample prepared by drop casting the semiconductor quantum dot dispersion liquid 1 on a Si substrate, sampling the resultant with a sampling knife, and mounting the specimen on a measurement stage. The other one was a sample prepared by forming a spin-coated film that had been subjected to ligand exchange with ethanedithiol, on a quartz glass substrate, and sampling the spin-coated film with a sampling knife in the same manner. That is, the latter sample is a semiconductor film obtained in the same manner as in the production of the semiconductor film of Comparative Example 1, except that a quartz glass substrate was used as the substrate.

Figure 9:
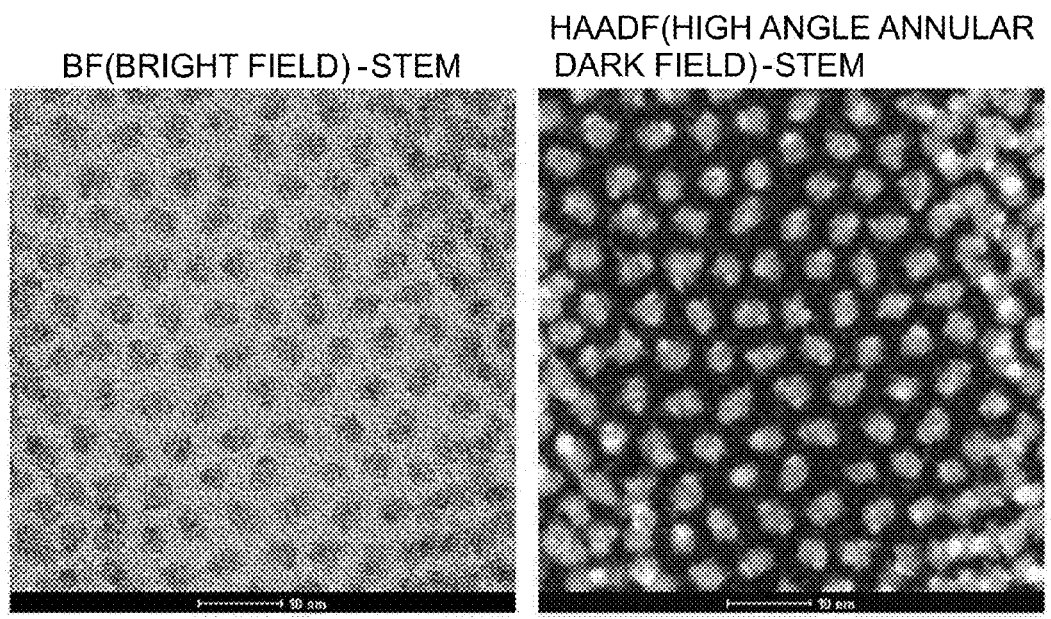
FIG. 9 is a TEM image showing a film formed using a semiconductor quantum dot dispersion liquid in which oleic acid is coordinated to semiconductor quantum dots (PbS).

FIG. 9 shows a TEM image obtained in the case of drop casting the semiconductor quantum dot dispersion liquid 1. It was confirmed from FIG. 9 that the average particle diameter (average of 10 particles) of the quantum dots was 3 nm. Also, it was found that since oleic acid, which is a long-chain fatty acid, is coordinated without ligand exchange, the distance between the semiconductor quantum dots was very broad (2 nm to 4 nm).

Figure 10:
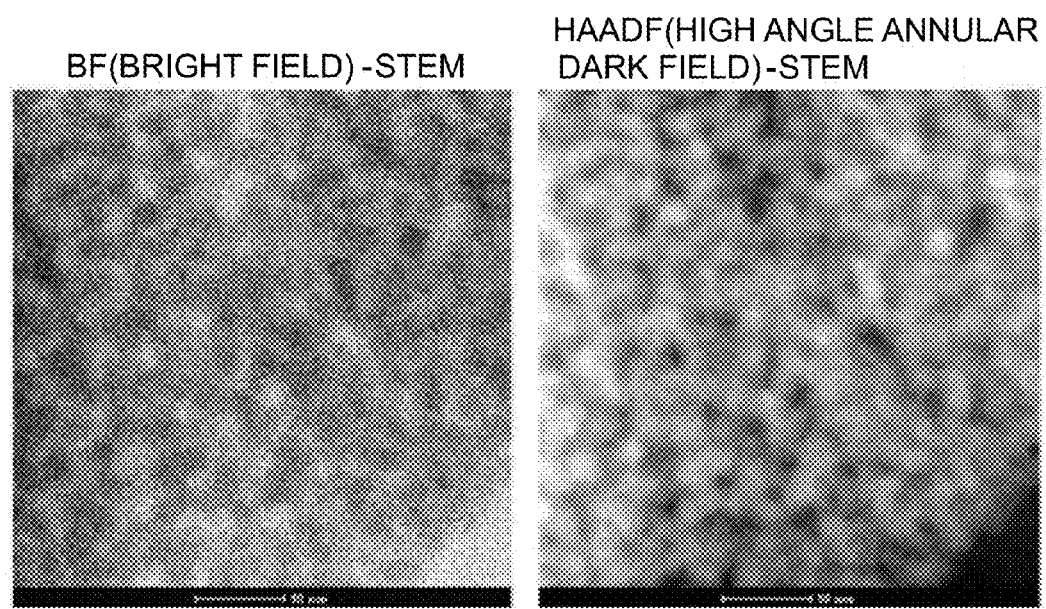
FIG. 10 is a TEM image showing a film produced by replacing oleic acid coordinated to semiconductor quantum dots (PbS) with ethanedithiol.

On the other hand, a TEM image of a spin-coated film that was subjected to ligand exchange is shown in FIG. 10. Although this is a semiconductor film to which ethanedithiol is coordinated having a value of Ip/Id that is not very high, it is understood that the distance between the semiconductor quantum dots is narrowed, and the semiconductor film shows a structure in which the semiconductor quantum dots are closely arranged. Therefore, it was confirmed that the main factor of an increase in the electrical conductivity in the semiconductor films of the invention, in which a particular ligand is coordinated to semiconductor quantum dots, is close proximity between the semiconductor quantum dots.

7. Average Shortest Interdot Distance between Semiconductor Quantum Dots in Semiconductor Film First, respective quantum dot films (samples) of Example 12, Example 13, Comparative Example 14, and Comparative Example 15 were produced as follows.

[Production of Semiconductor Film]

First, a hexamethyldisilazane solution was spin coated on a quartz glass plate, and hydrophobization of the surface was carried out. Then, a semiconductor film having an assembly of semiconductor quantum dots was prepared by the following procedure.

(I) Semiconductor Quantum Dot Assembly Forming Step

The semiconductor quantum dot dispersion liquid 3 prepared was drop cast, and thus a semiconductor quantum dot assembly film was obtained.

(II) Ligand Exchange Step

The semiconductor quantum dot assembly film was immersed for 3 minutes in a methanol solution of a ligand indicated in Table 3, and an exchange treatment from oleic acid as the first ligand to the ligand indicated in Table 3 was carried out. In this manner, quantum dot films of Examples and Comparative Examples were obtained.

(III) Washing Step i

Subsequently, each of the quantum dot films was immersed in a methanol solvent.

(IV) Washing Step ii

The quantum dot film obtained after the washing by the washing step i was further immersed in an octane solvent.

The series of steps (I) to (IV) were repeated for 2 cycles, and thus a semiconductor film having a thickness of 20 nm, which was composed of an assembly of PbS quantum dots and had been subjected to ligand exchange, was obtained.

In Comparative Example 15, a semiconductor quantum dot assembly film at the time point at which the (I) semiconductor quantum dot assembly forming step had been completed, was used.

For the quantum dot films (samples) of Example 12, Example 13, Comparative Example 14, and Comparative Example 15 thus obtained, a structure evaluation was carried out by the grazing incidence small angle X-ray scattering (GISAXS) method. Detection of scattered light was carried out by using Kα radiation of Cu as the incident light, irradiating the quantum dot film with X-radiation at an incident angle slightly larger than the total reflection angle (approximately 0.4°), and scanning with the detector in the in-plane direction.

Figure 11:
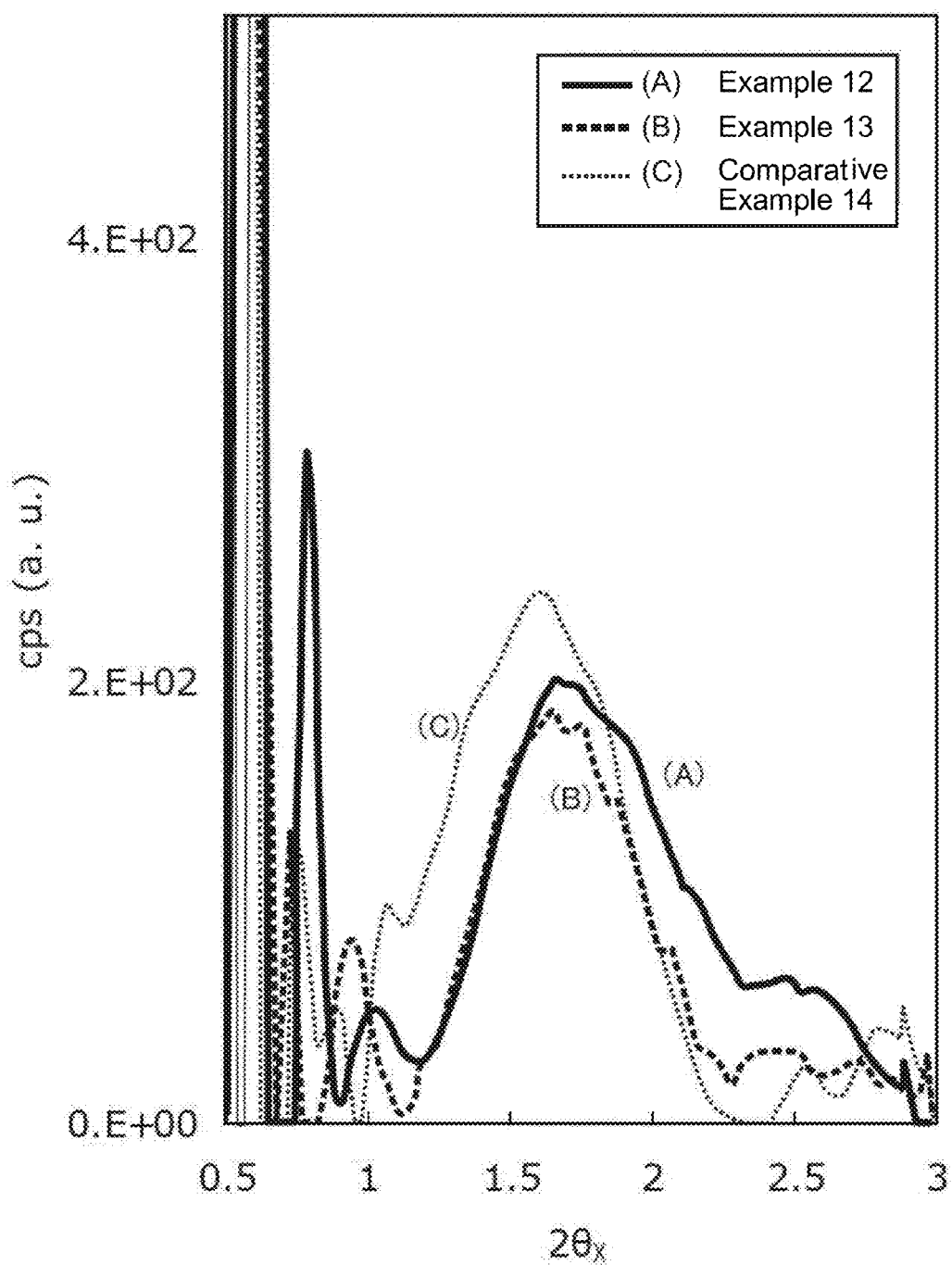
FIG. 11 is a diagram showing the in-plane angle dependency of scattered light in grazing incidence small angle X-ray scattering measurement carried out on the semiconductor films produced in the Examples and the Comparative Examples.

For the semiconductor film of Example 12, Example 13, and Comparative Example 14, the in-plane angle dependency of scattered light excluding the background structure of the scattered light for the respective ligand species is shown in FIG. 11.

As shown in FIG. 11 for the samples of Example 12, Example 13, and Comparative Example 14, while not shown in the diagram for Comparative Example 15, scattering peaks reflecting the in-plane periodic structure were obtained in all of the samples. Here, when a scattering peak position thus obtained is designated as $\theta_{MAX}$, the center-to-center distance d between semiconductor quantum dots in the sample is calculated by the following formula (D):

$$d = \lambda/2 \sin \theta_{MAX} \qquad (D).$$

In formula (D), λ represents the wavelength of the incident light.

Among the distances between adjacent quantum dots (distance obtained by subtracting the particle diameter of a quantum dot from the measured center-to-center distance d between quantum dots) as calculated from the scattering peaks, the shortest distance is indicated in Table 3. Meanwhile, the detected scattered light is the average of scattered X-radiation for a sample existing over the entire region irradiated with X-radiation in the measurement apparatus.

TABLE 3

| | Ligand | Average shortest interdot distance |
|---|---|---|
| Example 12 | 2-Aminoethane-1-thiol | 0.14 nm |
| Example 13 | 2-Aminoethanol | 0.29 nm |
| Comparative Example 14 | Ethanedithiol | 0.45 nm |
| Comparative Example 15 | Oleic acid (untreated) | 1.31 nm |

It can be seen from Table 3 that in the films that were subjected to a ligand exchange treatment for the oleic acid as the initial ligand (first ligand) (Example 12, Example 13, and Comparative Example 14), the quantum dot distance (distance between quantum dots) was decreased in all cases. Particularly, it was confirmed that in regard to the particular ligand represented by Formula (A), such as 2-aminoethane-1-thiol or 2-aminoethanol, close proximity between the semiconductor quantum dots is much higher compared with the conventional ethanedithiol-coordinated films.

From these results of close proximity between semiconductor quantum dots and the results of measuring electrical conduction as indicated in Table 1, it was found that when the average shortest interdot distance is smaller (less than 0.45 nm) than that of a conventional semiconductor film to which ethanedithiol is coordinated, a high photoelectric current value and a high dark current value are obtained. Furthermore, while significant film flaking was recognized by visual inspection in a semiconductor film to which ethanedithiol is coordinated, film flaking was not recognized in the semiconductor films of the Examples to which the particular ligand is coordinated, and satisfactory roughness was realized.

From the results shown above, it was found that basically, a quantum dot semiconductor film having a small average shortest interdot distance can realize high electrical conductivity. It was found that in order to obtain reliably high electrical conductivity without depending on the form of coordination of the ligand to the semiconductor quantum dots, the average shortest interdot distance is preferably less than 0.3 nm, and more preferably, it is preferable that the average shortest interdot distance is less than 0.2 nm as in the case of 2-aminoethane-1-thiol coordination.

All publications, patent applications, and technical standards mentioned in this specification are herein incorporated by reference to the same extent as if each individual publication, patent application, or technical standard was specifically and individually indicated to be incorporated by reference.

What is claimed is:

1. A semiconductor film, comprising:
   an assembly of semiconductor quantum dots containing a metal atom; and
   at least one ligand that is coordinated to the semiconductor quantum dots and that is selected from the group consisting of a ligand represented by the following Formula (A), a ligand represented by the following Formula (B), and a ligand represented by the following Formula (C):

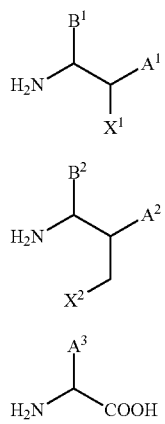

Formula (A)

Formula (B)

Formula (C)

wherein, in Formula (A), $X^1$ represents —SH, —NH$_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH;

in Formula (B), $X^2$ represents —SH, —NH$_2$, or —OH; and each of $A^2$ and $B^2$ independently represents a hydrogen atom or a substituent having from 1 to 10 atoms;

in Formula (C), $A^3$ represents a hydrogen atom or a substituent having from 1 to 10 atoms; and the semiconductor quantum dots have an average shortest interdot distance of less than 0.45 nm.

2. The semiconductor film according to claim 1, wherein each of $A^1$, $B^1$, $A^2$, $B^2$, and $A^3$ independently represents a hydrogen atom or a substituent having 7 or fewer atoms.

3. The semiconductor film according to claim 1, wherein $A^1$, $B^1$, $A^2$, $B^2$, and $A^3$ are hydrogen atoms.

4. The semiconductor film according to claim 1, wherein the at least one ligand is at least one selected from the group consisting of 2-aminoethanethiol, 2-aminoethanol, 3-amino-1-propanol, a 2-aminoethanethiol derivative, a 2-aminoethanol derivative, and a 3-amino-1-propanol derivative.

5. The semiconductor film according to claim 1, wherein the at least one ligand is represented by Formula (A) and forms a 5-membered ring chelate together with the metal atom in the semiconductor quantum dots.

6. The semiconductor film according to claim 1, wherein a complex stability constant log $\beta_1$ between the at least one ligand and the metal atom of the semiconductor quantum dots is 8 or higher.

7. The semiconductor film according to claim 1, wherein the semiconductor quantum dots have an average shortest interdot distance of less than 0.30 nm.

8. The semiconductor film according to claim 1, wherein the semiconductor quantum dots have an average shortest interdot distance of less than 0.20 nm.

9. The semiconductor film according to claim 1, wherein the semiconductor quantum dots contain at least one selected from the group consisting of PbS, PbSe, InN, InAs, InSb, and InP.

10. The semiconductor film according to claim 9, wherein the semiconductor quantum dots contain PbS.

11. The semiconductor film according to claim 1, wherein the semiconductor quantum dots have an average particle diameter of from 2 nm to 15 nm.

12. A solar cell, comprising the semiconductor film according to claim 1.

13. A light-emitting diode, comprising the semiconductor film according to claim 1.

14. A thin film transistor, comprising the semiconductor film according to claim 1.

15. An electronic device, comprising the semiconductor film according to claim 1.

16. A method of producing the semiconductor film of claim 1, the method comprising:
    a semiconductor quantum dot assembly forming step of applying, onto a substrate, a semiconductor quantum dot dispersion liquid containing semiconductor quantum dots containing a metal atom, a first ligand coordinated to the semiconductor quantum dots, and a first solvent, and thereby forming an assembly of the semiconductor quantum dots; and
    a ligand exchange step of applying, to the assembly of the semiconductor quantum dots, a solution containing a second solvent and a second ligand that has a shorter molecular chain length than the first ligand and that is at least one selected from the group consisting of a ligand represented by the following Formula (A), a ligand represented by the following Formula (B), and a ligand represented by the following Formula (C), and thereby exchanging the first ligand coordinated to the semiconductor quantum dots with the second ligand:

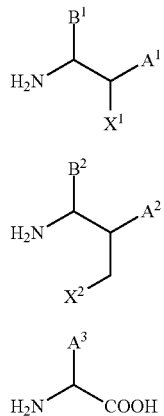

Formula (A)

Formula (B)

Formula (C)

wherein, in Formula (A), $X^1$ represents —SH, —$NH_2$, or —OH; and each of $A^1$ and $B^1$ independently represents a hydrogen atom or a substituent having from 1 to 10 atoms; provided that when $A^1$ and $B^1$ are both hydrogen atoms, $X^1$ represents —SH or —OH;

in Formula (B), $X^2$ represents —SH, —$NH_2$, or —OH; and each of $A^2$ and $B^2$ independently represents a hydrogen atom or a substituent having from 1 to 10 atoms; and in Formula (C), $A^3$ represents a hydrogen atom or a substituent having from 1 to 10 atoms.

17. The method of producing a semiconductor film according to claim 16, wherein the first ligand is a ligand having a main chain having 6 or more carbon atoms.

18. The method of producing a semiconductor film according to claim 16, wherein each of the semiconductor quantum dot assembly forming step and the ligand exchange step is carried out two or more times.

19. The method of producing a semiconductor film according to claim 16, wherein each of $A^1$, $B^1$, $A^2$, $B^2$, and $A^3$ independently represents a hydrogen atom or a substituent having 7 or fewer atoms.

20. The method of producing a semiconductor film according to claim 16, wherein $A^1$, $B^1$, $A^2$, $B^2$, and $A^3$ are hydrogen atoms.

21. The method of producing a semiconductor film according to claim 16, wherein the second ligand is at least one selected from the group consisting of 2-aminoethanethiol, 2-aminoethanol, 3-amino-1-propanol, a 2-aminoethanethiol derivative, a 2-aminoethanol derivative, and a 3-amino-1-propanol derivative.

22. The method of producing a semiconductor film according to claim 16, wherein, in the ligand exchange step, the second ligand is represented by Formula (A) and forms a 5-membered ring chelate together with the metal atom in the semiconductor quantum dots.

23. The method of producing a semiconductor film according to claim 16, wherein the semiconductor quantum dots contain at least one selected from the group consisting of PbS, PbSe, InN, InAs, InSb, and InP.

24. The method of producing a semiconductor film according to claim 23, wherein the semiconductor quantum dots contain PbS.

25. The method of producing a semiconductor film according to claim 16, wherein the semiconductor quantum dots have an average particle diameter of from 2 nm to 15 nm.

* * * * *